US011285230B2

(12) United States Patent
Kopalli

(10) Patent No.: US 11,285,230 B2
(45) Date of Patent: Mar. 29, 2022

(54) METHODS AND SYSTEMS FOR FLUSHING A MEDICAL GAS FLOW SYSTEM

(71) Applicant: GE Precision Healthcare LLC, Milwaukee, WI (US)

(72) Inventor: Chandra Aloke Kopalli, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 227 days.

(21) Appl. No.: 16/551,578

(22) Filed: Aug. 26, 2019

(65) Prior Publication Data

US 2021/0060197 A1 Mar. 4, 2021

(51) Int. Cl.
*A61L 2/20* (2006.01)
*A61L 2/22* (2006.01)
*C09K 3/30* (2006.01)

(52) U.S. Cl.
CPC *A61L 2/20* (2013.01); *A61L 2/22* (2013.01); *A61M 2202/02* (2013.01); *A61M 2209/10* (2013.01); *C09K 3/30* (2013.01)

(58) Field of Classification Search
CPC ........ A61L 2/20; A61L 2/22; A61M 2209/10; C09K 3/30
See application file for complete search history.

(56) References Cited

U.S. PATENT DOCUMENTS

| | | | |
|---|---|---|---|
| 3,481,689 A | 12/1969 | Rosdahl et al. | |
| 5,256,371 A | 10/1993 | Pippert | |
| 9,937,275 B2 | 4/2018 | Cadieux et al. | |
| 10,610,902 B1 * | 4/2020 | Brook | B05B 7/0483 |
| 2018/0353632 A1 * | 12/2018 | Divisi | A61L 9/14 |

FOREIGN PATENT DOCUMENTS

| | | | |
|---|---|---|---|
| CN | 206120790 U * | 4/2017 | |
| JP | 5371439 B2 | 9/2013 | |
| WO | 2007069922 A1 | 6/2007 | |
| WO | 2016086350 A1 | 6/2016 | |

OTHER PUBLICATIONS

English Translation of Document No. CN 206120790 U provided by the European Patent Office espacenet.com: Zhang Jun; Multi-Purpose Anesthesia Machine, Breathing Machine Return Circuit Sterilizing Machine; Apr. 26, 2017 (Year: 2017).*

* cited by examiner

*Primary Examiner* — Kevin Joyner
(74) *Attorney, Agent, or Firm* — McCoy Russell LLP

(57) ABSTRACT

Various methods and systems are provided for flushing a medical gas flow system. In one embodiment, a method for a medical gas flow system comprises: performing a disinfecting cycle of a ventilation gas path comprising a plurality of gas flow passages by: flowing gas from a pressurized gas source of the medical gas flow system to a liquid disinfectant reservoir of a flush module; combining the gas with a liquid disinfectant stored within the liquid disinfectant reservoir to form a disinfectant aerosol; and flowing the disinfectant aerosol through the plurality of gas flow passages.

15 Claims, 7 Drawing Sheets

METHODS AND SYSTEMS FOR FLUSHING A MEDICAL GAS FLOW SYSTEM

FIELD

Embodiments of the subject matter disclosed herein relate to medical gas flow systems, and more particularly, to medical ventilatory systems.

BACKGROUND

A medical gas flow system, such as a medical ventilatory system, may include a plurality of gas passages and other components adapted to flow gases to a subject from one or more gas sources. The one or more gas sources may include oxygen, nitrogen, and/or air maintained at a pressure above atmospheric air pressure. Each gas source may be coupled to an inlet of the system, and the gases may come into contact with surfaces of the gas passages and other components of the system as the gases flow through the system to the subject. Exhalation gases of the subject may flow from the subject through the gas passages and may be collected at an outlet of the system. A portion of the exhalation gases may flow back into system upstream of the subject and may mix and/or converge with gases from the one or more gas sources.

BRIEF DESCRIPTION

In one embodiment, a method for a medical gas flow system comprises: performing a disinfecting cycle of a ventilation gas path comprising a plurality of gas flow passages by: flowing gas from a pressurized gas source of the medical gas flow system to a liquid disinfectant reservoir of a flush module; combining the gas with a liquid disinfectant stored within the liquid disinfectant reservoir to form a disinfectant aerosol; and flowing the disinfectant aerosol through the plurality of gas flow passages. In this way, the ventilation gas path may be disinfected and/or cleaned without disassembling the medical gas flow system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 1 is a perspective view of a medical gas flow system including a flush module according to an embodiment of the invention.

FIG. 2 is a block diagram of a medical gas flow system including a flush module according to an exemplary embodiment of the invention.

FIG. 3 is a block diagram of the medical flow system of FIG. 2 illustrating a cleaning and/or disinfecting flow path of the flush module.

FIG. 4 is a flowchart illustrating a method for cleaning and/or disinfecting a gas flow path of a medical gas flow system including a flush module according to an embodiment of the invention.

FIG. 5 is a flowchart illustrating a method for cleaning a gas flow path of a medical gas flow system including a flush module according to an embodiment of the invention.

FIG. 6 is a flowchart illustrating a method for disinfecting a gas flow path of a medical gas flow system including a flush module according to an embodiment of the invention.

FIG. 7 is a block diagram of a medical gas flow system including a flush module according to another exemplary embodiment of the invention.

DETAILED DESCRIPTION

The following description relates to various embodiments for flushing a medical gas flow system. A medical gas flow system, such as the system shown by FIG. 1 and the system shown by FIG. 7, includes a plurality of gas passages adapted to flow gases to a subject from a gas source. As the gases flow through the system via the gas passages (similar to the flow shown schematically by FIG. 2), the gases may come into contact with surfaces of the gas passages and other components such as valves. A portion of the gases may be inhaled by the subject, and the exhalation gases of the subject may return to the system where the exhalation gases may mix and/or converge with gases from gas source. As the exhalation gases flow through the gas passages and other components, a likelihood of debris accumulation and/or biological contamination of the gas passages and other components may be increased. As a result, cleaning of the surfaces of the gas passages and other components may be desired in order to reduce a likelihood of obstruction of the gas passages by debris and/or biological contaminants such as microbes. However, conventional cleaning of the surfaces includes removing the gas passages and other components from the medical gas flow system in order to separately clean each component at a location external to the medical gas flow system. The medical gas flow system may be disassembled during removal of the gas passages and other components, resulting in an increased maintenance time and/or cost of the medical gas flow system. Additionally, disassembly and reassembly of the medical gas flow system may increase a likelihood of degradation of the components of the medical gas flow system resulting from transport and/or handling of the components.

In order to address the above issues, the medical gas flow system of the present disclosure includes a flush module adapted to clean and/or disinfect the components of the medical gas flow system without disassembly and reassembly of the gas passages. The flush module may be utilized to perform cleaning and/or disinfecting of a gas path of the medical gas flow system, as illustrated by the flowchart of FIG. 4. The flush module receives gas from the gas source, and the gas drives a cleaning fluid and/or a disinfecting fluid from the flush module through the gas passages of the medical gas flow system. The cleaning fluid and/or disinfecting fluid may flow through at least the gas passages adapted to receive exhalation gases from the subject, as shown by the example cleaning fluid and/or disinfecting fluid flow path of FIG. 3. The flush module may include one or more reservoirs adapted to store liquid cleaning fluid and/or liquid disinfecting fluid. The flush module may separate the liquid cleaning fluid and/or liquid disinfecting fluid into small droplets in order to mix the liquid cleaning fluid and/or liquid disinfecting fluid with the gas from the gas source. The mixture may flow through the gas passages of the medical gas flow system without disassembly of the medical gas flow system in order to clean and/or disinfect the gas passages and other components.

After performing one or more cleaning cycles (as described below with reference to FIG. 5) or performing one or more disinfecting cycles (as described below with reference to FIG. 6), the flush module may additionally flow water through the gas passages and other components in order to reduce a likelihood of residual cleaning fluid and/or disinfecting fluid being retained within the gas passages. Gas from the gas source may then flow through the gas passages in order to remove residual water from the gas passages. In this way, the medical gas flow system may be cleaned and/or disinfected without disassembly of the medical gas flow system, and the maintenance time and/or cost of the medical gas flow system may be decreased.

Figure 1:
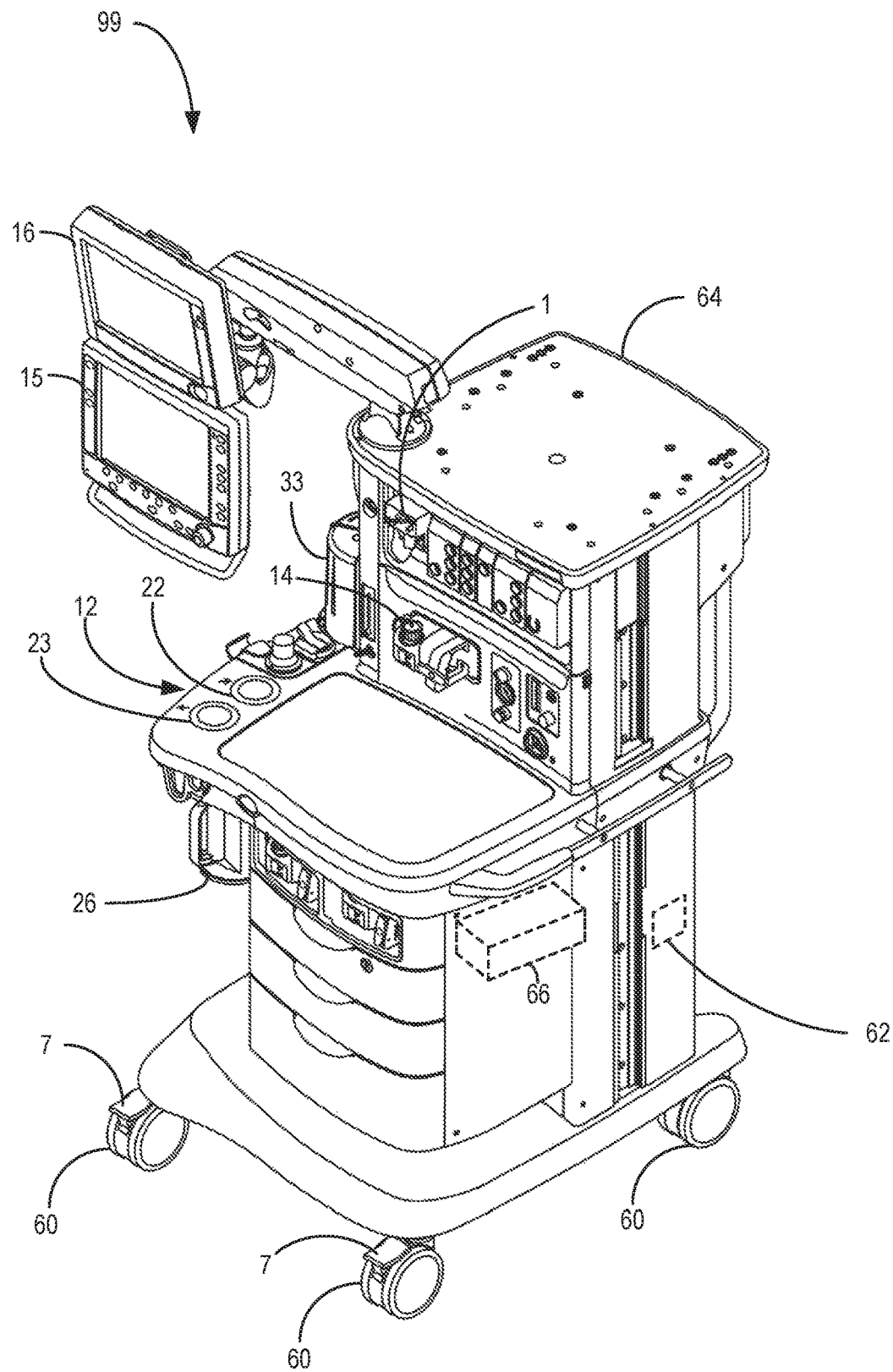

FIG. 1 shows a medical gas flow system 99 including a flush module 66 (shown schematically in FIG. 1) from a side perspective view. The medical gas flow system 99 may be described herein as an anesthesia machine. Anesthesia machine 99 includes a frame 64 supported by casters 60, where the movement of the casters may be controlled (e.g., stopped) by one or more locks 7. In some examples, the frame 64 may be formed of a plastic material (e.g., polypropylene). In other examples, the frame 64 may be formed from a different type of material (e.g., metal, such as steel).

Anesthesia machine 99 also includes respiratory gas module 1, ventilator 12 (explained in more detail below), vaporizer 14 (explained in more detail below), anesthesia display device 15, and patient monitoring display device 16.

Vaporizer 14 may be in the form of a removable cassette such that a supply of anesthetic agent can be removed from the cassette and such that different types of anesthetic agents can be supplied to the anesthesia machine by simply removing the cassette and replacing it with a different cassette for a different anesthetic agent. The vaporizer 14 includes a housing having a drug reservoir that contains a supply of anesthetic agent to be delivered to a patient. The drug reservoir may have a discharge opening formed in a back wall of the housing that is configured to receive a discharge tube (not shown), which is part of the anesthesia machine, forming a gas-tight seal for delivery of anesthetic vapor to a patient.

Vaporizer 14 may include at least one absorbent wick within the reservoir. A passageway allows fresh gas from a gas source to pass to the absorbent wick(s). Vaporized liquid from the absorbent wick(s) and accompanying fresh gas may flow to the back of the drug reservoir and out the discharge opening in the housing. A lower portion of the drug reservoir may contain the liquid anesthetic agent and an upper portion of the reservoir may contain the vaporized anesthetic agent and breathing gases. During operation, a combination of temperature and pressure affect the liquid anesthetic agent and cause it to vaporize into the breathing gases. The gases carrying the vaporized agent are then discharged through the discharge opening.

A rear of the anesthesia machine 99 may include one or more pipeline connections to facilitate coupling of the anesthesia machine to pipeline gas sources. Additionally, the rear of the anesthesia machine may include a cylinder yoke, via which one or more gas-holding cylinders may be coupled to the anesthesia machine. Thus, through the pipeline connection and/or cylinder connections, gas may be provided to the anesthesia machine, where the gas may include but is not limited to fresh gas, oxygen, and nitrous oxide. The gas that enters the anesthesia machine may mix with the vaporized anesthetic agent at the vaporizer, as described above, and be supplied to a patient via the ventilator. In some embodiments, the rear of the anesthesia machine may also include a serial port, a collection bottle connection, cylinder wrench storage, anesthesia gas scavenging system, main power inlet, system circuit breaker, equipotential stud, outlet circuit breaker, and isolated electrical outlet.

The ventilator 12 may include an expiratory check valve 22, inspiratory check valve 23, absorber canister 26, and bellows assembly 33. When a patient breathing circuit is coupled to the ventilator, the breathing gases (e.g., fresh gas, oxygen, and/or nitrous oxide mixed with vaporized anesthetic agent) exit the machine from an inspiratory port (which may be positioned at the same location as the inspiratory check valve 23) and travel to a patient. Expiratory gases from the patient re-enter the anesthesia machine via an expiratory port (which may be positioned at the same location as the expiratory check valve 22), where the carbon dioxide may be removed from the expiratory gases via the absorber canister 26.

During operation of the vaporizer 14, an operator (e.g., an anesthesiologist) may adjust an amount of vaporized anesthetic agent that is supplied to a patient by adjusting a flow rate of gases from the gas source(s) (e.g., the gas pipelines) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of the anesthesia machine 99. In one example, a first flow control valve may be positioned between the gas source(s) and the vaporizer 14 and may be actuatable via the flow adjustment devices to a fully opened position, a fully closed position, and a plurality of positions between the fully opened position and the fully closed position.

The anesthesia machine may additionally include one or more bypass valves configured to bypass gases from the gas source(s) around the vaporizer 14. The bypass valves may enable a first portion of gases flowing from the gas source to flow directly from the gas source to the inspiratory port, and a second portion of gases flowing from the gas source may flow through the vaporizer 14 to mix with the vaporized anesthetic agents prior to flowing to the inspiratory port. By adjusting a ratio of an amount of gases flowing to the port via the bypass valves relative to an amount of gases flowing to the port via the vaporizer 14, the operator may control a concentration of vaporized anesthetic agent in gases at the port.

Further, the adjustments described above may be facilitated at least in part based on output from the respiratory gas module 1. Respiratory gas module 1 may be configured to measure various parameters of the gases exiting the vaporizer and/or being provided to the patient. For example, respiratory gas module 1 may measure the concentrations of carbon dioxide, nitrous oxide, and anesthesia provided to the patient. Further, respiratory gas module 1 may measure respiration rate, minimum alveolar concentration, patient oxygen, and/or other parameters. The output from the respiratory gas module 1 may be displayed via a graphical user interface displayed on a display device (e.g., device 15 and/or 16) and/or used by the controller to provide closed-loop feedback control of the amount of anesthesia provided to the patient.

Ventilator 12 may optionally be coupled to a breathing circuit (not shown) including a plurality of tubes (e.g., gas passages). The breathing circuit may be coupled between an airway of a patient (e.g., via a breathing mask positioned to enclose the mouth and/or nose of the patient) and the inspiratory port. Gases (e.g., oxygen, or a mixture of oxygen and vaporized anesthetic agents from vaporizer 14) may flow from the port, through the breathing circuit, and into the airway of the patient, where the gases are absorbed by the lungs of the patient. By adjusting the concentration of vaporized anesthetic agent in the gases as described above, the operator may adjust an amount by which the patient is anesthetized.

During conditions in which the breathing circuit is coupled to the airway, anesthetic agent and/or fresh gases may flow into the airway (e.g., be inhaled by the patient) via the inspiratory check valve 23. For example, inspiratory check valve 23 may open automatically (e.g., without input or adjustment by the operator) in response to inhalation of the patient, and may close automatically in response to exhalation of the patient. Similarly, the expiratory check valve 22 may open automatically in response to exhalation of the patient, and may close automatically in response to inhalation of the patient.

In some examples, the operator may alternately and/or additionally control one or more operating parameters of the anesthesia machine 99 via an electronic controller 62 of the anesthesia machine 99 (shown schematically by FIG. 1). Controller 62 includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor. Controller 62 may be communicatively (e.g., wired or wirelessly) coupled to one or more external or remote computing devices, such as a hospital computing system, and may be configured to send and receive various information, such as electronic medical record information, procedure information, and so forth. As described below, controller 62 may control operation of the flush module 66 in order to perform one or more cleaning cycles, disinfecting cycles, flush cycles, etc. of a gas path of the anesthesia machine 99.

The controller receives signals from the various sensors of the anesthesia machine 99 and employs the various actuators of the anesthesia machine 99 to adjust operation of the anesthesia machine 99 based on the received signals and instructions stored on the memory of the controller. For example, the flow of gases to the inspiratory port may be controlled via an input device (e.g., keyboard, touchscreen, etc.) coupled to the electronic controller of the anesthesia machine 99. The controller may be electrically coupled to display device 15 and/or 16 in order to display operating parameters of the anesthesia machine 99. The controller may receive signals (e.g., electrical signals) via the input device and may adjust operating parameters of the anesthesia machine 99 in response (e.g., responsive) to the received signals. For example, the operator may input a desired flow rate of gases (e.g., oxygen) flowing from the gas source to the patient and/or vaporizer 14.

A corresponding valve position of one or more valves of the anesthesia machine (e.g., a position of one or more bypass valves, as described above) may be empirically determined and stored in a predetermined lookup table or function on the controller. For example, the controller may receive the desired flow rate of gases via the input device and may determine an amount of opening of the one or more bypass valves corresponding to the desired flow rate based on the lookup table, with an input being the desired flow rate and an output being the valve position. The controller may transmit an electrical signal to an actuator of the valve in order to adjust the valve position. In some examples, the controller may compare the desired flow rate of gases to a measured flow rate of gases as measured by a flow rate sensor (e.g., an inspiratory flow sensor).

Controller 62 is shown in FIG. 1 for illustrative purposes, and it is to be understood that controller 62 may be located internally of anesthesia machine 99 and thus may not be visible externally on anesthesia machine. Controller 62 may include multiple devices/modules that may be distributed across anesthesia machine 99.

Figure 2:
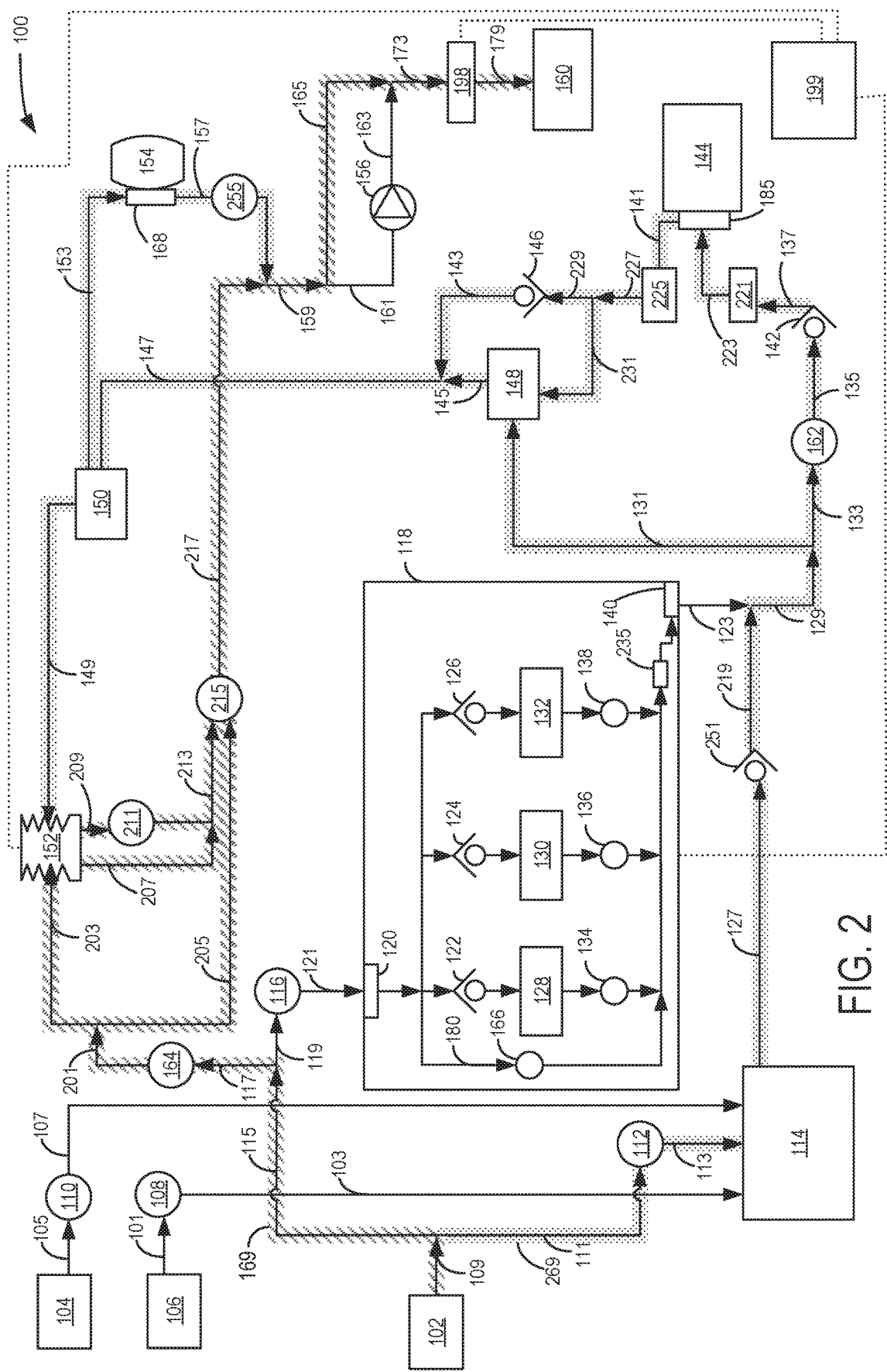

FIG. 2 illustrates a block diagram of a medical gas flow system 100 including a flush module 118 according to an exemplary embodiment. The medical gas flow system 100 may be similar to anesthesia machine 99 described above with reference to FIG. 1 and may be referred to herein as a medical ventilatory system or anesthesia machine. The flush module 118 may be similar to the flush module 66 described above. The medical gas flow system 100 is adapted to provide inhalation gases to a subject (e.g., a patient) via a patient breathing apparatus 144 (e.g., a respirator). The medical gas flow system 100 includes a first gas source 102, a second gas source 104, and a third gas source 106. In the embodiment shown, the first gas source 102 may include pressurized oxygen or air (e.g., first gas source 102 may be a canister adapted to maintain air and/or oxygen at a pressure higher than atmospheric air pressure, such as 25 psi above atmospheric air pressure), and the second gas source 104 and third gas source 106 may each include a different gas than the first gas source 102 (e.g., nitrogen). Gas from first gas source 102 may be referred to herein as inhalation gas. Pressurized gas from first gas source 102 may flow through gas passage 109 during conditions in which a valve fluidly coupled to the first gas source 102 (e.g., first gas source valve 112, which may be referred to herein as a flow meter valve, flush module inlet valve 116, or ventilator bypass valve 164) is partially opened or fully opened. Similarly, pressurized gas from second gas source 104 may flow through gas passage 105 during conditions in which second gas source valve 110 fluidly coupled to gas passage 105 is partially opened or fully opened, and pressurized gas from third gas source 106 may flow through gas passage 101 during conditions in which third gas source valve 108 fluidly coupled to gas passage 101 is partially opened or fully opened.

In other embodiments, the medical gas flow system 100 may include a different gas source configuration. For example, in some embodiments, the medical gas flow system 100 may be utilized as a ventilator, wherein the air and oxygen are mixed prior to being delivered to a patient. The mixed gas may be pressurized. As one example, a blower may be included in order to pressurize the mixed gases (e.g., similar to the embodiment shown by FIG. 7 and described below). As another example, a pressurized air supply may be used with a regulator and proportional solenoid valve to control the pressure of the mixed gas. Sensors in the flow path may determine the amounts of the individual gases as well as the amount of the mixed gas. Pressure sensors may determine the airway pressure and ensure that desired pressures are delivered to the patient. A pressurized oxygen supply (or the pressurized air supply) may be utilized to perform flush cycles, with a bypass path included to flow the cleaning agent (e.g., detergent) and disinfection agent (e.g., disinfectant). The ventilator exhalation path includes the patient gas flow circuit, and the patient gas flow circuit includes a flow sensor that may be cleaned and/or disinfected via the cleaning agent and disinfection agent.

The flush module 118 is adapted to provide cleaning and/or disinfecting of the various gas passages and other components of the medical gas flow system 100 during conditions in which the medical gas flow system 100 is not flowing gas to a subject (e.g., a patient) for inhalation. The flush module 118 may provide the cleaning and/or disinfecting of the gas passages and other components without disassembly of the medical gas flow system 100. Specifically, during cleaning and/or disinfecting via the flush module 118, each of the gas passages of the medical gas flow system 100 may be maintained in the same position and coupled configuration used to flow gas to the subject for inhalation, such that the cleaning and/or disinfecting occurs without any of the gas flow passages being removed from the medical gas flow system 100. In this way, the flush module 118 may provide the cleaning and/or disinfecting of at least a subset of the same gas passages used to flow exhalation gases from the subject. In some embodiments, the flush module 118 may provide cleaning and/or disinfecting to all of the same gas passages used to flow exhalation gases from the subject. Additionally, in some embodiments, the flush module 118 may provide the cleaning and/or disinfecting to at least a subset of the same gas passages used to provide gas to the subject for inhalation. Further, in some embodiments, an operator of the medical gas flow system 100 (e.g., a clinician) may easily initiate one or more cycles of the flush module (e.g., cleaning cycles, flush cycles, disinfecting cycles, and/or drying cycles) via a user interface device (e.g., computer graphical user interface, one or more switches and/or buttons of a control panel of the flush module 118, etc.) controlled by an electronic controller 199 of the medical gas flow system 100.

The medical gas flow system 100 includes electronic controller 199 adapted to control the operation of various components of the medical gas flow system 100. Dotted lines illustrate the electrical coupling of the controller 199 to each of flush module 118 and VOC sensor 198. However, although not illustrated by dotted lines, the controller 199 may be further electrically coupled to other components of the medical gas flow system 100 (e.g., valves of the medical gas flow system 100) in order to control operation of the components.

First gas source 102 may be fluidly coupled to vaporizer 114 via gas passage 109, gas passage 111, first gas source valve 112, and gas passage 113. Second gas source 104 may be fluidly coupled to vaporizer 114 via gas passage 105, second gas source valve 110, and gas passage 107. Third gas source 106 may be fluidly coupled to vaporizer 114 via gas passage 101, third gas source valve 108, and gas passage 103. The vaporizer 114 may receive gas from one or more of the first gas source 102, second gas source 104, and third gas source 106 and may be controlled by the controller 199 in order to output a desired gas mixture to gas passage 127. For example, gas output by the vaporizer 114 to gas passage 127 may be a mixture of gases from two or more of the first gas source 102, second gas source 104, and third gas source 106 (e.g., a mixture of pure oxygen and air), or the gas output by the vaporizer 114 to gas passage 127 may be a gas from only one of first gas source 102, second gas source 104, and third gas source 106 (e.g., pure oxygen from first gas source 102). The vaporizer 114 may additionally include anesthetic agents for mixing with the gases received by the vaporizer 114 via the gas passage 103, gas passage 107, and/or gas passage 113, and the controller 199 may transmit electrical signals to the vaporizer 114 in order to adjust the amount of anesthetic agent mixed with the gas output by the vaporizer at gas passage 127 (e.g., increase or decrease a concentration of the anesthetic agent). Gas passage 127 may include check valve 251 in order to reduce a likelihood of backflow of gas through gas passage 219 to the vaporizer 114.

The controller 199 receives signals from various sensors of the medical gas flow system of FIG. 2 and employs various actuators of the components of the medical gas flow system of FIG. 2 to adjust operation of the medical gas flow system based on the received signals and instructions stored on a memory of the controller. For example, the electronic controller 199 may transmit electrical signals to an actuator of first gas source valve 112 in order to adjust a position (e.g., an amount of opening) of first gas source valve 112. As one example, the controller 199 may transmit an electrical signal having a first pulse width to the actuator of first gas source valve 112 in order to adjust the first gas source valve 112 to the fully opened position (e.g., a position in which pressurized gas flows from first gas source 102 through first gas source valve 112 to gas passage 113), and the controller 199 may transmit an electrical signal having a second pulse width to the actuator of first gas source valve 112 in order to adjust the first gas source valve 112 to a fully closed position (e.g., a position in which gas does not flow from first gas source 102 through the first gas source valve 112 to gas passage 113). The controller 199 may additionally transmit electrical signals to the actuator of first gas source valve 112 in order to adjust first gas source valve 112 to a plurality of positions between the fully opened position and fully closed position, with the pulse width of the electrical signals being based on a calculation using a look-up table stored in non-transitory memory of the controller (e.g., with the input being the amount of opening of the first gas source valve 112 and the output being electrical pulse width).

Although operation of first gas source valve 112 via controller 199 is described herein as one example, controller 199 may individually control operation of each valve of medical gas flow system 100 in a similar way (e.g., controller 199 may transmit electrical signals to a corresponding actuator of each valve in order to adjust the amount of opening of each valve independently of each other valve). For example, the controller 199 may adjust a position of flush module inlet valve 116 to a fully closed position, fully opened position, or a plurality of positions between the fully closed position and fully opened position in order to control a flow of gas from first gas source 102 to flush module 118. Further, controller 199 may determine (e.g., measure) an amount of opening of each valve of the medical gas flow system 100 based on electrical signals received by the controller 199 from each valve and/or one or more corresponding sensors of the medical gas flow system 100 (e.g., mass flow sensors). For example, controller 199 may determine an amount of opening of first gas source valve 112 based on an amount of gas flowing through the first gas source valve 112, with the amount of gas flowing through first gas source valve 112 determined via a calculation or look-up table stored in non-transitory memory of the controller. An input of the calculation or look-up table may be a measured gas flow rate downstream of the first gas source valve 112, where the gas flow rate is measured by the controller via electrical signals transmitted to the controller 199 by a mass flow sensor (not shown) positioned downstream of the first gas source valve 112.

As another example, controller 199 may receive electrical signals from components of the flush module 118 and may transmit electrical signals to the components of flush module 118 in order to control operation of the flush module 118 (e.g., perform a cleaning and/or disinfecting routine of the medical gas flow system 100 via flush module 118). For example, controller 199 may adjust an amount of opening of one or more of first reservoir valve 134, second reservoir valve 136, and third reservoir valve 138 of flush module 118 in order to adjust an output of the flush module 118 (e.g., adjust an amount of cleaning fluid, disinfectant fluid, and/or water flowing from outlet 140 of the flush module 118 to gas passage 123). Example operations of the flush module 118 are described further below.

In the embodiment shown, medical gas flow system 100 includes vaporizer 114, absorber 148, switch 150, adjustable pressure-limiting (APL) valve 255, bag 154, bellows 152, and volatile organic compound (VOC) sensor 198. Gases from first gas source 102, second gas source 104, and/or third gas source 106 may flow through the various gas passages of the medical gas flow system 100, and a portion of the gases may be scavenged via scavenging system 160. In some embodiments, scavenging system 160 may be a hospital ventilation system configured to dispose of waste gases and/or other fluids flowing from the medical gas flow system 100 (e.g., exhalation gases of the subject flowing from patient breathing apparatus 144 and/or excess gases from first gas source 102, second gas source 104, and/or third gas source 106). In some embodiments, scavenging system 160 may flow a portion of gases output by the medical gas flow system 100 back into one or more inlets of the medical gas flow system 100 (e.g., in order to recirculate the gases back through the medical gas flow system 100). For example, scavenging system 160 may be fluidly coupled to gas passage 103, gas passage 107, and/or gas passage 111 via one or more valves such that the controller 199 may adjust operation of the one or more valves in order to adjust an amount of gas flowing from scavenging system 160 back into the gas passage 103, gas passage 107, and/or gas passage 111.

In some embodiments, vacuum may be applied to an outlet of the medical gas flow system 100 in order to increase a flow rate of fluids through the gas passages to the scavenging system 160. The controller 199 may energize pump 156 in order to generate vacuum (e.g., decreased pressure relative to atmospheric air pressure) at an outlet of the medical gas flow system 100 (e.g., gas passage 179 fluidly coupled to the scavenging system 160). Producing vacuum at the outlet reduces a flow resistance within the gas passages in the direction of the outlet and may increase the flow rate (e.g., flow velocity) of fluids flowing through the gas passages. For example, during conditions in which the controller 199 initiates a cleaning cycle (as described below with reference to FIG. 5), disinfecting cycle (as described below with reference to FIG. 6), or flush cycle of the medical gas flow system 100 via the flush module 118, the controller 199 may energize the pump 156 in order to increase the flow rate of fluids (e.g., gases from first gas source 102, second gas source 104, and/or third gas source 106, and/or aerosols produced by flush module 118) through the gas passages of the medical gas flow system 100 (e.g., gas passages forming a ventilation gas path of the medical gas flow system 100, such as the shaded gas path 171 shown by FIG. 3).

During some conditions, such as conditions in which the controller 199 performs a cleaning cycle, flush cycle, and/or disinfecting cycle via the flush module 118 as described below, the controller 199 may not flow gas from any of the first gas source 102, second gas source 104, and third gas source 106 through the vaporizer 114. Instead, the controller 199 may move each of third gas source valve 108, second gas source valve 110, and first gas source valve 112 to the fully closed position such that gas does not flow to the vaporizer 114 from gas passage 103, gas passage 107, and gas passage 113. However, while not flowing gas to the vaporizer 114 as described above, the controller 199 may move flush module inlet valve 116 and/or ventilator bypass valve 164 (which may be referred to herein as an inspiratory flow control valve) to a partially opened position or the fully opened position in order to flow gas from first gas source 102 through the gas passages of the medical gas flow system 100 and bypass the vaporizer 114.

In the embodiment shown by FIG. 2, third gas source valve 108, second gas source valve 110, and flush module inlet valve 116 are each in the fully closed position, and ventilator bypass valve 164 may be in a partially opened position or the fully opened position. In this configuration, gas does not flow from third gas source 106 or second gas source 104 to vaporizer 114. However, gas may flow from first gas source 102 along the gas path indicated by shaded path 169. Specifically, at least a portion of gas from first gas source 102 may bypass the vaporizer 114 by flowing from first gas source 102 through gas passage 109, gas passage 115 (which may be referred to herein as a vaporizer bypass passage), gas passage 117, ventilator bypass valve 164, and gas passage 201. The shaded path 169 does not include gas flow through gas passage 119, and in the conditions described above, gas does not flow to the flush module 118 from first gas source 102. However, during conditions in which flush module inlet valve 116 is moved to a partially opened position or the fully opened position, gas may additionally or alternatively flow through gas passage 119, flush module inlet valve 116, and gas passage 121 to bypass vaporizer 114 (as described below with reference to FIG. 3).

As indicated by shaded path 169 in FIG. 2, gas from first gas source 102 may flow through ventilator bypass valve 164, gas passage 201, gas passage 203 to bellows 152, and gas passage 205 to exhalation valve 215. The gas flowing to bellows 152 may flow through the bellows 152 to gas passage 207 and gas passage 209, with gas passage 207 fluidly coupled to exhalation valve 215, and with gas passage 209 fluidly coupled to pop-off valve 211. Pop-off valve 211 is fluidly coupled to exhalation valve 215 via gas passage 213. Pop-off valve 211 may be configured to open during conditions in which a pressure of gas within the bellows 152 exceeds a threshold pressure (e.g., 20 psi). Pop-off valve 211 may additionally be configured to open during conditions in which a cleaning cycle and/or disinfecting cycle is performed (e.g., to enable detergent and/or disinfectant to flow through the pop-off valve 211). Gas flowing to exhalation valve 215 may then flow through gas passage 217 to scavenging system 160 via gas passage 159, gas passage 165, gas passage 173, and gas passage 179. In some embodiments, gas flowing from exhalation valve 215 may additionally flow through gas passage 161, pump 156, and gas passage 163 to scavenging system 160.

During some conditions, such as conditions in which first gas source valve 112 is in a partially opened position or fully opened position, gas may flow from the first gas source 102 through the vaporizer 114, as indicated by shaded path 269. Gas flowing through the vaporizer 114 flows through gas passage 127, check valve 251, gas passage 219, and gas passage 129. A portion of the gas may flow through gas passage 131 to absorber 148 (e.g., absorber canister). Absorber 148 may absorb carbon dioxide ($CO_2$) flowing through the gas passages of the medical gas flow system 100 (e.g., due to exhalation gases from the subject flowing through the patient breathing apparatus 144 and through at least a subset of the gas passages such as gas passage 141, gas passage 147, and/or gas passage 159, the exhalation gases being returned to the medical gas flow system 100 via scavenging system 160, as described above). Absorber 148 may include a CO2 absorbent (e.g., soda lime) to absorb CO2 from gas flowing to the absorber 148 (e.g., before recirculation of the gas to the patient). CO2 may be generated by respiration of the patient, and the CO2 may be routed to bellows 152. During the following inspiratory phase, the gas from the bellows 152 may recirculate through the CO2 absorbent of the absorbent and the CO2 of the gas may be reduced before it is delivered to the patient.

The controller 199 may adjust the position of inhalation flow valve 162 in order to adjust an amount of gases flowing to the absorber 148. For example, fully opening the inhalation flow valve 162 may decrease the amount of gases flowing to absorber 148 and may increase the amount of gases flowing from gas passage 129 to gas passage 133 and gas passage 135. Fully closing or partially closing the inhalation flow valve 162 may increase the amount of gases flowing to absorber 148 and decrease the amount of gases flowing from gas passage 129 to gas passage 133 and gas passage 135. Accordingly, as indicated by the shaded path 269, during conditions in which the inhalation flow valve 162 is partially opened or fully opened, gas may flow from first gas source 102 through gas passage 133, inhalation flow valve 162, gas passage 135, check valve 142, gas passage 137, inspiratory flow sensor 221, gas passage 223, coupler 185, gas passage 141, expiratory flow sensor 225, gas passage 227, gas passage 229, check valve 146, and gas passage 143. In this configuration, at least a portion of the gases from first gas source 102 may bypass the absorber 148 and may flow to the subject via patient breathing apparatus 144 coupled to gas passage 223 and gas passage 141 by coupler 185 (e.g., for inhalation by the subject). In some embodiments, all of the gases from the first gas source 102 may bypass the absorber 148 and flow to the subject via the patient breathing apparatus 144 as described above. Further, in some embodiments, a portion of gas may flow through coupler 185, gas passage 141, gas passage 227, and gas passage 231 to absorber 148.

Gases flowing from the absorber 148 via gas passage 145 and gases flowing from the subject via the patient breathing apparatus 144 to gas passage 143 may mix and/or converge and flow through gas passage 147 to switch 150. During conditions in which all of the gas from first gas source 102 flows through the absorber 148, the gas may flow to the switch 150 through gas passage 145 and gas passage 147 and may not flow to the switch 150 from gas passage 143. During conditions in which all of the gas from first gas source 102 flows to the patient at patient breathing apparatus 144 as described above, the gas may flow to the switch 150 through gas passage 143 and gas passage 147 and may not flow to the switch 150 from gas passage 145 (e.g., from the outlet of the absorber 148).

Switch 150 may be controlled by the controller 199 in order to enable gas flow from gas passage 147 to one or both of gas passage 149 and gas passage 153. For example, the controller 199 may adjust the switch 150 to a first position in which gas flows from gas passage 147 to gas passage 153 and does not flow from gas passage 147 to gas passage 149. Controller 199 may additionally adjust the switch 150 to a second position in which gas flows from gas passage 147 to gas passage 149 and does not flow from gas passage 147 to gas passage 153. The controller 199 may additionally adjust the switch 150 to a third position in which gas flows from gas passage 147 to each of gas passage 149 and gas passage 153. The shaded path 269 shown by FIG. 2 indicates that the switch 150 is in the third position. However, in some embodiments, the switch 150 may be adjusted to any of the first, second, or third position.

In the configuration shown by FIG. 2, gas flows from the switch 150 through gas passage 153 to a coupler 168 fluidly coupled to bag 154. Bag 154 may be compressed by an operator of the medical gas flow system 100 (e.g., a clinician) in order to manually drive gas through the gas passages of the medical gas flow system 100 (e.g., flow gas through gas passage 153 and gas passage 157 if a pressure of the gas exceeds a threshold pressure of the APL valve 255 in order to adjust APL valve 255 to an opened position). However, during some conditions (e.g., during a cleaning cycle as described below with reference to FIG. 5, disinfecting cycle as described below with reference to FIG. 6, and/or flush cycle), the bag 154 may be blocked (e.g., fluidly isolated from coupler 168) such that gas does not flow through the bag 154 and instead bypasses the bag 154.

As described above, during some conditions (e.g., conditions in which the switch 150 is in the second or third position), gas may flow from the switch 150 through gas passage 149. Gas flowing through gas passage 149 in such conditions may flow through bellows 152, bypassing the bag 154. The bellows 152 may be controlled by controller 199 in some embodiments. A pressure of gas within gas path 203 may actuate ventilator bypass valve 164 to flow gas through gas passage 201. Bag 154 may be manually compressed by a clinician in some examples (e.g., by hand, or by using another device such as a foot petal) The bag 154 may operate without input from the controller 199 in some embodiments (e.g., without actuation via the controller 199).

Gas flowing through gas passage 157 (e.g., through coupler 168) and/or gas passage 217 (e.g., through bellows 152) may flow through gas passage 159. During conditions in which pump 156 is not energized (e.g., turned off), the flow of gas from gas passage 159 through gas passage 161 may be reduced, and the flow of gas through gas passage 165 may be increased. During conditions in which the pump 156 is energized by the controller 199 (e.g., turned on by the controller 199 in order to increase the flow rate of gases through the gas passages, as described above), an increased amount of gas may flow from gas passage 159 through gas passage 161, pump 156, and gas passage 163, and a reduced amount of gas may flow from gas passage 159 through gas passage 165.

Gas flowing through gas passage 163 and/or gas passage 165 flows into gas passage 173. The gas flowing through gas passage 173 flows across VOC sensor 198, through gas passage 179, and to the scavenging system 160. As described above, VOC sensor 198 may detect (e.g., measure) a concentration of VOCs within gas flowing through the gas passage 173. VOC sensor 198 may be configured to detect different organic compounds based on a diffraction of light through the gas flowing through the VOC sensor 198, in some embodiments (e.g., via gas chromatography). The controller 199 may determine the concentration of different compounds within the gas flowing through the VOC sensor 198 based an output signal of the VOC sensor 198. The VOC sensor 198 may house a filter to trap gases (or particular compounds of the gases) flowing through the scavenged gas path, in some embodiments.

Figure 3:
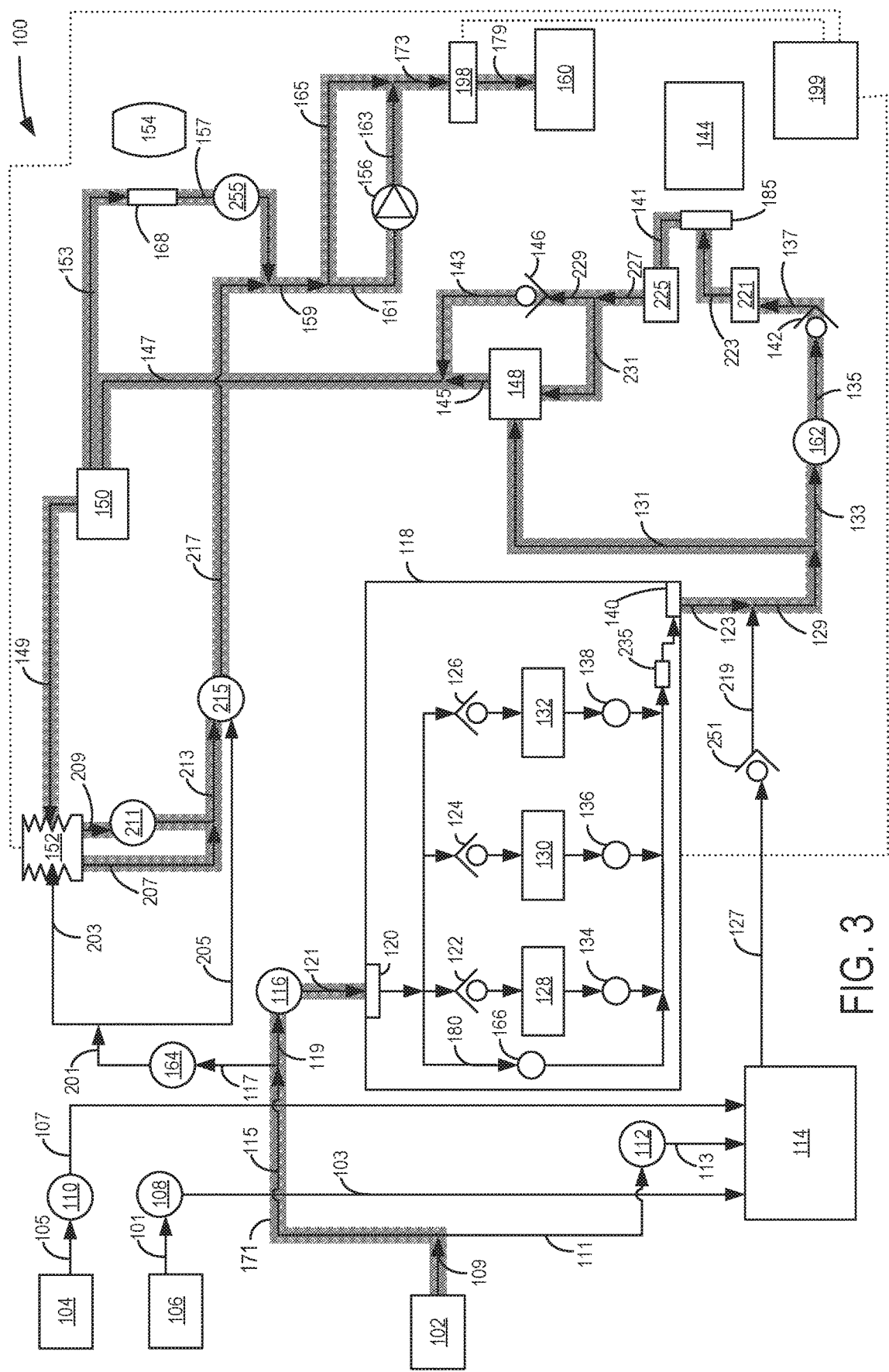

Turning now to FIG. 3, shaded gas path 171 is shown to indicate an alternative gas path of the medical gas flow system 100. The shaded path 169 and shaded path 269 shown by FIG. 2 and the shaded gas path 171 shown by FIG. 3 may each be referred to herein as ventilation gas paths of the medical gas flow system 100. However, the shaded gas path 171 shown by FIG. 3 includes gas flow to flush module 118, while the shaded path 169 and shaded path 269 shown by FIG. 2 each bypass gas flow to flush module 118.

As indicated by the shaded gas path 171 shown by FIG. 3, gas flows from first gas source 102 through gas passage 109, gas passage 115, gas passage 119, flush module inlet valve 116, and gas passage 121 to inlet 120 of flush module 118. In the configuration shown, first gas source valve 112 and ventilator bypass valve 164 may be in the fully closed position, and flush module inlet valve 116 may be in the fully opened position. As a result, the flow of gas from the pressurized gas source (e.g., first gas source 102) bypasses the vaporizer 114 via vaporizer bypass passage 115 and flows through the flush module 118 to gas passage 123 (e.g., such that the gas from first gas source 102 does not flow through the vaporizer 114). In some embodiments, ventilator bypass valve 164 and/or flush module inlet valve 116 may be in a partially opened position such that a portion of gas from first gas source 102 flows through each of ventilator bypass valve 164 and flush module inlet valve 116.

Gas flowing to the inlet 120 of the flush module 118 may flow to one or more of bypass gas passage 180, first liquid reservoir 128, second liquid reservoir 130, and third liquid reservoir 132. Check valve 122 is coupled between first liquid reservoir 128 and inlet 120 to reduce a likelihood of fluid backflow from first liquid reservoir 128 to inlet 120, check valve 124 is coupled between second liquid reservoir 130 and inlet 120 to reduce a likelihood of fluid backflow from second liquid reservoir 130 to inlet 120, and check valve 126 is coupled between third liquid reservoir 132 and inlet 120 to reduce a likelihood of fluid backflow from third liquid reservoir 132 to inlet 120. In some embodiments, first liquid reservoir 128 may be a detergent reservoir configured to store liquid detergent (e.g., Prolystica® 2× Concentrate Enzymatic Presoak and Cleaner), second liquid reservoir 130 may be a water reservoir configured to store liquid water, and third liquid reservoir 132 may be a disinfectant reservoir configured to store liquid disinfectant (e.g., CIDEX® OPA Solution).

Each of the first liquid reservoir 128, second liquid reservoir 130, and third liquid reservoir 132 may be refillable reservoirs, in some embodiments. In other embodiments, one or more of the first liquid reservoir 128, second liquid reservoir 130, and third liquid reservoir 132 may be removable cartridges having a pre-defined volume of liquid stored therein (e.g., liquid detergent, liquid water, and liquid disinfectant, respectively). In yet other embodiments, the flush module 118 may instead include a single liquid reservoir adapted to store one of liquid detergent, liquid water, or liquid disinfectant, and the liquid stored within the single reservoir may be removed and/or filled by the operator of the medical gas flow system 100 (e.g., a clinician) according to a desired use (e.g., filled with liquid detergent to perform a cleaning cycle, filled with water to perform a flush cycle, or filled with liquid disinfectant to perform a disinfecting cycle). With regard to the method 200 described below with reference to FIG. 4, for example, the single container may be filled with liquid detergent prior to performing a cleaning cycle, then emptied and filled with water prior to performing a flush cycle immediately following the cleaning cycle, then emptied and filled with disinfected prior to performing a disinfecting cycle immediately following the flush cycle.

Each of the first liquid reservoir 128, second liquid reservoir 130, and third liquid reservoir 132 may be coupled to a corresponding mesh 235 adapted to separate liquid into droplets (e.g., atomize the liquid into a mist). Although a single mesh 235 is shown in FIGS. 2-3, in some embodiments, first liquid reservoir 128 may be coupled to a first mesh adapted to atomize liquid detergent stored in the first liquid reservoir 128 into a mist during conditions in which pressurized gas from the first gas source 102 flows to the first liquid reservoir 128, second liquid reservoir 130 may be coupled to a second mesh adapted to atomize water stored in the second liquid reservoir 130 into a mist during conditions in which pressurized gas from the first gas source 102 flows to the second liquid reservoir 130, and third liquid reservoir 132 may be coupled to a third mesh adapted to atomize liquid disinfectant stored in the third liquid reservoir 132 into a mist during conditions in which pressurized gas from the first gas source 102 flows to the third liquid reservoir 132. However, in the embodiment shown, mesh 235 is a single mesh configured to atomize liquid from the first liquid reservoir 128, second liquid reservoir 130, and third liquid reservoir 132 during conditions in which pressurized gas from the first gas source 102 is supplied to one of the first liquid reservoir 128, second liquid reservoir 130, and third liquid reservoir 132, respectively.

In order to flow gas from first gas source 102 to first liquid reservoir 128, the controller 199 may adjust first reservoir valve 134 to a partially opened position or fully opened position. In order to flow gas from first gas source 102 to second liquid reservoir 130, the controller 199 may adjust second reservoir valve 136 to a partially opened position or fully opened position. In order to flow gas from first gas source 102 to third liquid reservoir 132, the controller 199 may adjust third reservoir valve 138 to a partially opened position or fully opened position. During some conditions, gas from first gas source 102 may flow to only one of the first liquid reservoir 128, second liquid reservoir 130, or third liquid reservoir 132. For example, during a cleaning cycle (as described below with reference to FIG. 5), first reservoir valve 134 may be partially opened or fully opened by the controller 199 while second reservoir valve 136 and third reservoir valve 138 are fully closed by the controller 199 in order to flow gas from first gas source 102 to first liquid reservoir 128 and not to second liquid reservoir 130 or third liquid reservoir 132. Similarly, during a flush cycle, controller 199 may flow gas only to second liquid reservoir 130 and not first liquid reservoir 128 or third liquid reservoir 132. During a disinfecting cycle, controller 199 may flow gas only to third liquid reservoir 132 and not to first liquid reservoir 128 or second liquid reservoir 130.

During some conditions, the controller may partially open or fully open bypass valve 166 in order to flow gas from gas source 102 through bypass gas passage 180. For example, the controller 199 may fully close first reservoir valve 134, second reservoir valve 136, and third reservoir valve 138, with bypass valve 166 being partially or fully opened, in order to flow gas through bypass gas passage 180 and bypass valve 166 and to not flow gas to the first liquid reservoir 128, second liquid reservoir 130, and third liquid reservoir 132 (e.g., during a drying cycle and/or while flowing gas in bursts or pulses, as described below with reference to FIGS. 5-6).

In the embodiment shown by FIG. 3, gas does not flow to the patient breathing apparatus 144 and instead bypasses the patient breathing apparatus 144 via coupler 185, with coupler 185 flowing gas from gas passage 223 to gas passage 141. In this configuration, the coupler 185 is fluidly isolated from patient breathing apparatus 144. Further, gas does not flow to bag 154 and instead bypasses the bag 154 via coupler 168, with coupler 168 flowing gas from gas passage 153 to gas passage 157 (e.g., with the coupler 168 fluidly isolated from the bag 154). Shaded gas path 171 additionally includes gas passage 133, inhalation flow valve 162, gas passage 135, check valve 142, gas passage 137, inspiratory flow sensor 221, gas passage 223, coupler 185, gas passage 141, expiratory flow sensor 225, gas passage 227, gas passage 229, gas passage 231, check valve 146, and gas passage 143. In some embodiments, shaded gas path 171 includes gas passage 149, bellows 152, gas passage 207, gas passage 209, pop-off valve 211, gas passage 213, exhalation valve 215, and gas passage 217 (e.g., by adjusting the position of switch 150 via controller 199). Further, in some embodiments, shaded gas path 171 includes gas passage 161, pump 156, and gas passage 163 (e.g., by energizing pump 156).

The shaded gas path 171 indicates a path of fluids output by the flush module 118. For example, the controller 199 may flow pressurized gas from first gas source 102 to the first liquid reservoir 128, with the first liquid reservoir 128 configured to store liquid detergent. The pressurized gas may drive the liquid detergent through the mesh 235 coupled to the first liquid reservoir 128 in order to atomize the liquid detergent into a mist, and the atomized liquid detergent mist may mix and/or converge with the pressurized gas to form a detergent aerosol (e.g., the detergent mist may be entrained by the pressurized gas). The detergent aerosol may be driven out of the outlet 140 of the flush module 118 via the pressure of the pressurized gas from the first gas source 102 and may flow through the ventilation gas path indicated by shaded gas path 171, downstream of outlet 140. The outlet 140 is positioned downstream of vaporizer 114, such that fluids (e.g., gas and/or aerosols) flowing from the outlet 140 to the plurality of gas flow passages do not flow from the outlet 140 to the vaporizer 114. The detergent may flow through the medical gas flow system 100 without disassembly of the medical gas flow system 100. Water aerosol (e.g., from flowing pressurized gas to second liquid reservoir 130 configured to store water) and/or disinfectant aerosol (e.g., from flowing pressurized gas to third liquid reservoir 132 configured to store liquid disinfectant) may be output by the flush module 118 in a similar way, with each aerosol flowing along the shaded gas path 171 to flush and disinfect (respectively) the gas passages of the medical gas flow system 100. Example cleaning cycles (e.g., output of detergent aerosol by the flush module 118), flush cycles (e.g., output of water aerosol by the flush module 118), and disinfecting cycles (e.g., output of disinfectant aerosol by the flush module 118) are described in further detail below with reference to FIGS. 4-6.

Figure 4:
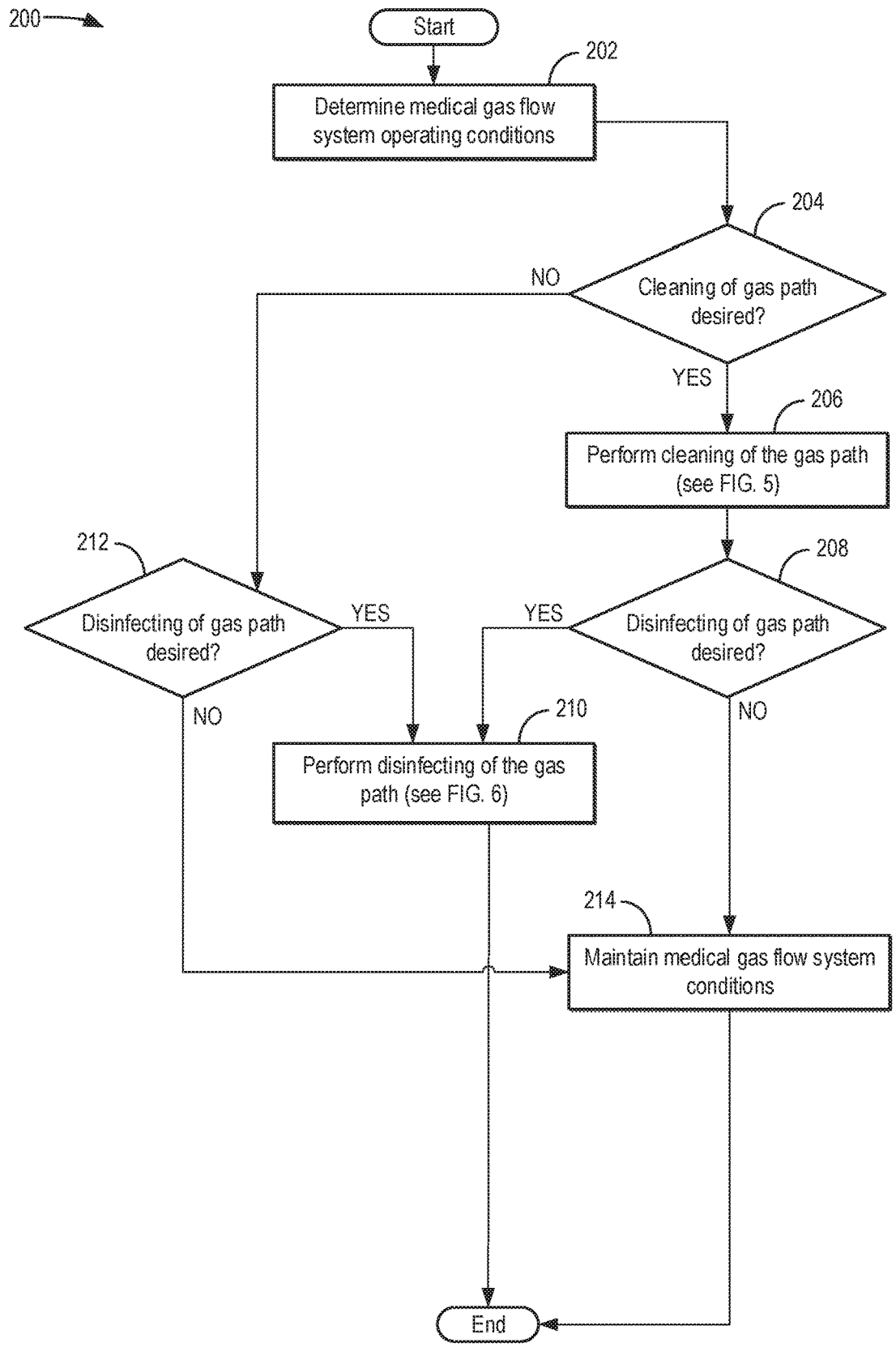

FIG. 4 shows a flowchart illustrating a method 200 for performing cleaning and/or disinfecting of a gas flow path of a medical gas flow system including a flush module according to an embodiment of the disclosure. Method 200 may be carried out according to instructions stored in non-transitory memory of a controller of the medical gas flow system, such as controller 199 shown by FIGS. 2-3. Accordingly, the medical gas flow system in which method 200 is implemented may be a non-limiting example of the anesthesia machine 99 shown by FIG. 1 and/or the medical gas flow system 100 shown by FIGS. 2-3 and described above, the gas flow path may be a non-limiting example of the ventilation shaded gas path 171 shown by FIG. 2 and described above, and the flush module may be a non-limiting example of the flush module 66 shown by FIG. 1 and/or the flush module 118 shown by FIGS. 2-3 and described above. Components described herein with reference to method 200 may be the same as those described herein with reference to method 400 shown by FIG. 5 and method 500 shown by FIG. 6. (e.g., in some embodiments, method 400 and method 500 may each be included within method 200 and may reference the same components as those described herein with regard to method 200).

At 202, medical gas flow system operating conditions are determined.

Medical gas flow system operating conditions may include gas flow rates, flow path direction, valve positions (e.g., amount of valve opening), VOC concentration, etc. For example, VOC concentration may be determined by an electronic controller of the medical gas flow system via electrical signals output to the controller by a VOC sensor. In some embodiments, the electronic controller may be similar to controller 199 shown by FIGS. 2-3 and described above, and the VOC sensor may be similar to VOC sensor 198 shown by FIGS. 2-3 and described above.

At 204, a determination is made of whether cleaning of the gas path is desired. In some embodiments, cleaning of the gas path may be desired during conditions in which an output of the VOC sensor is greater than a threshold output. Cleaning may be desired during conditions in which the gas path has previously been used to provide respiration gases to a first patient and prior to using the gas path to provide respiration gases to a different, second patient. Cleaning may reduce a likelihood bacterial cross-contamination between the first and second patient. As another example, cleaning may be desired during conditions in which an output of the VOC sensor is greater than a threshold output (e.g., the controller determines that a concentration of volatile organic compounds within the gas, as measured by the VOC sensor, is greater than a threshold concentration).

In other embodiments, cleaning may be desired during conditions in which a threshold amount of time has elapsed following a most recent cleaning cycle of the medical gas flow system, with a time of the most recent cleaning cycle stored in a memory of the controller. In yet other embodiments, cleaning may be desired during conditions in which the medical gas flow system has been decoupled from a first subject (e.g., a first patient) and has not yet been coupled to a second subject (e.g., a second patient). Coupling the medical gas flow system to the first or second subject may include flowing ventilation gases to the first or second subject via the gas path of the medical gas flow system (e.g., flowing gases to a patient breathing apparatus adapted to couple to a subject for inhalation of the gases, similar to the patient breathing apparatus 144 described above). In still further embodiments, it may be determined that cleaning is desired in response to user input requesting that a cleaning cycle be carried out.

If cleaning is desired, the controller controls the flush module to perform cleaning of the gas path at 206, as described in further detail below with reference to FIG. 5. Performing the cleaning of the gas path may include performing the one or more cleaning cycles and may additionally include performing one or more flush cycles and one or more drying cycles of the gas path.

A determination is made at 208 of whether disinfecting of the gas path is desired. In some embodiments, disinfecting may be desired during conditions in which a threshold amount of time has elapsed following a most recent disinfecting cycle of the medical gas flow system, with a time of the most recent disinfecting cycle stored in a memory of the controller. In some embodiments, disinfecting may be desired following a cleaning cycle, and the disinfecting may occur prior to providing respiration to a different patient via the medical gas flow system. In other embodiments, disinfecting may be desired during conditions in which the medical gas flow system has been decoupled from a first subject (e.g., a first patient) and has not yet been coupled to a second subject (e.g., a second patient). Coupling the medical gas flow system to the first or second subject may include flowing ventilation gases to the first or second subject via the gas path of the medical gas flow system (e.g., flowing gases to a patient breathing apparatus adapted to couple to a subject for inhalation of the gases, similar to the patient breathing apparatus 144 described above).

If disinfecting is not desired at 208, medical gas flow system conditions are maintained at 214. Maintaining the medical gas flow system conditions may include not performing cleaning cycles and not performing disinfecting cycles. Additionally, maintaining the medical gas flow system conditions may include maintaining a valve fluidly coupling the flush module to the pressurized gas source (e.g., flush module inlet valve 116 shown by FIGS. 2-3 and described above) in the fully closed position in order to bypass the flush module (e.g., to not flow pressurized gases to the flush module). Further, maintaining the medical gas flow system conditions may include maintaining a flow of gas from the pressurized gas source to a patient breathing apparatus or respirator (e.g., patient breathing apparatus 144 shown by FIGS. 2-3) while bypassing the flush module (e.g., not flowing gas from the pressurized gas source to the flush module).

Figure 6:
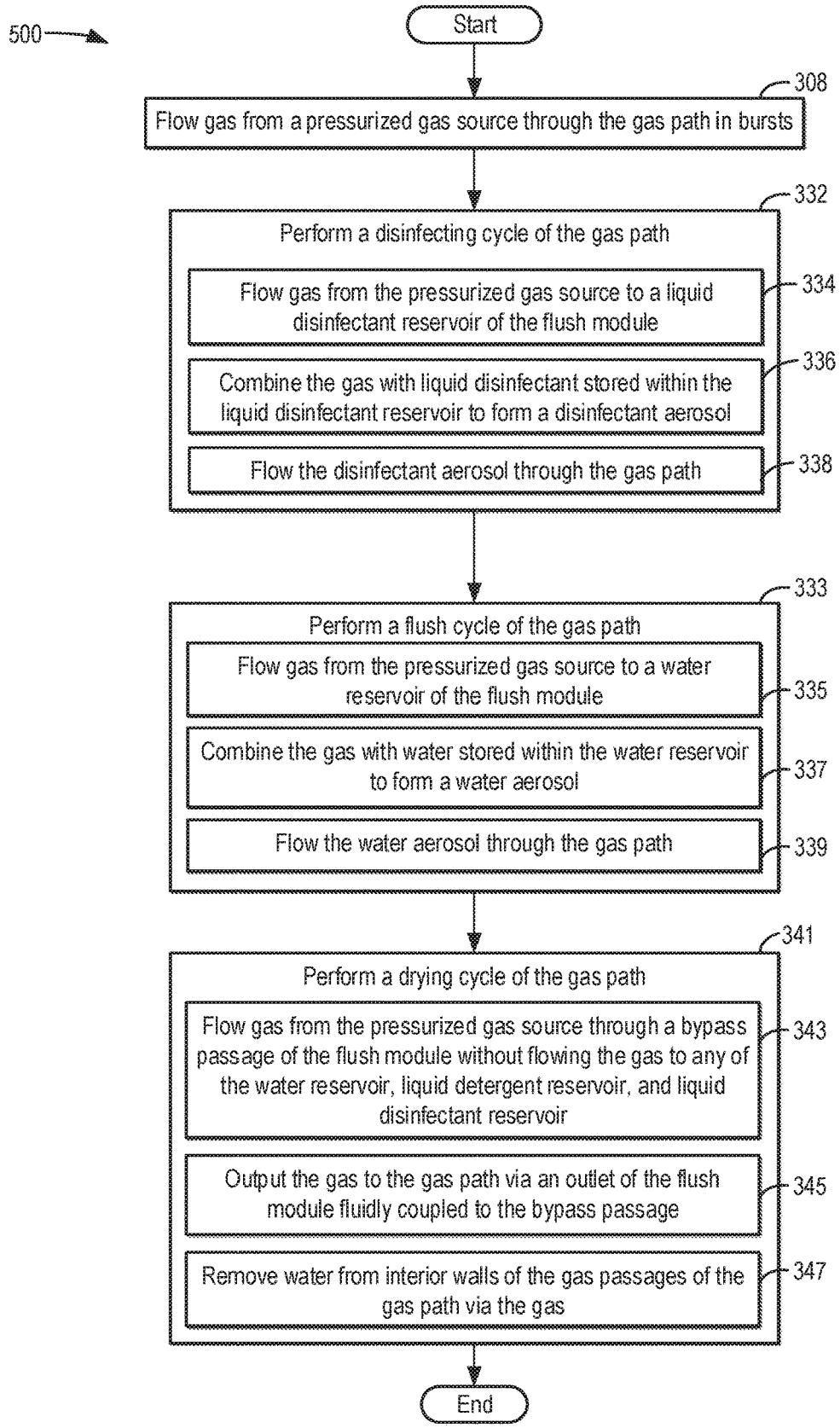

If disinfecting is desired at 208, the controller controls the flush module to perform disinfecting of the gas path at 210, as described in further detail below with reference to FIG. 6. Performing the disinfecting of the gas path may include performing the one or more disinfecting cycles and may additionally include performing one or more flush cycles and one or more drying cycles of the gas path.

If cleaning of the gas path is not desired at 204, a determination is made at 212 of whether disinfecting of the gas path is desired. The determination at 212 may be similar to the determination at 208. If disinfecting of the gas path is desired at 212, the controller controls the flush module to perform disinfecting of the gas path at 210. However, if disinfecting of the gas path is not desired at 212, the medical gas flow system conditions are maintained at 214.

Figure 5:
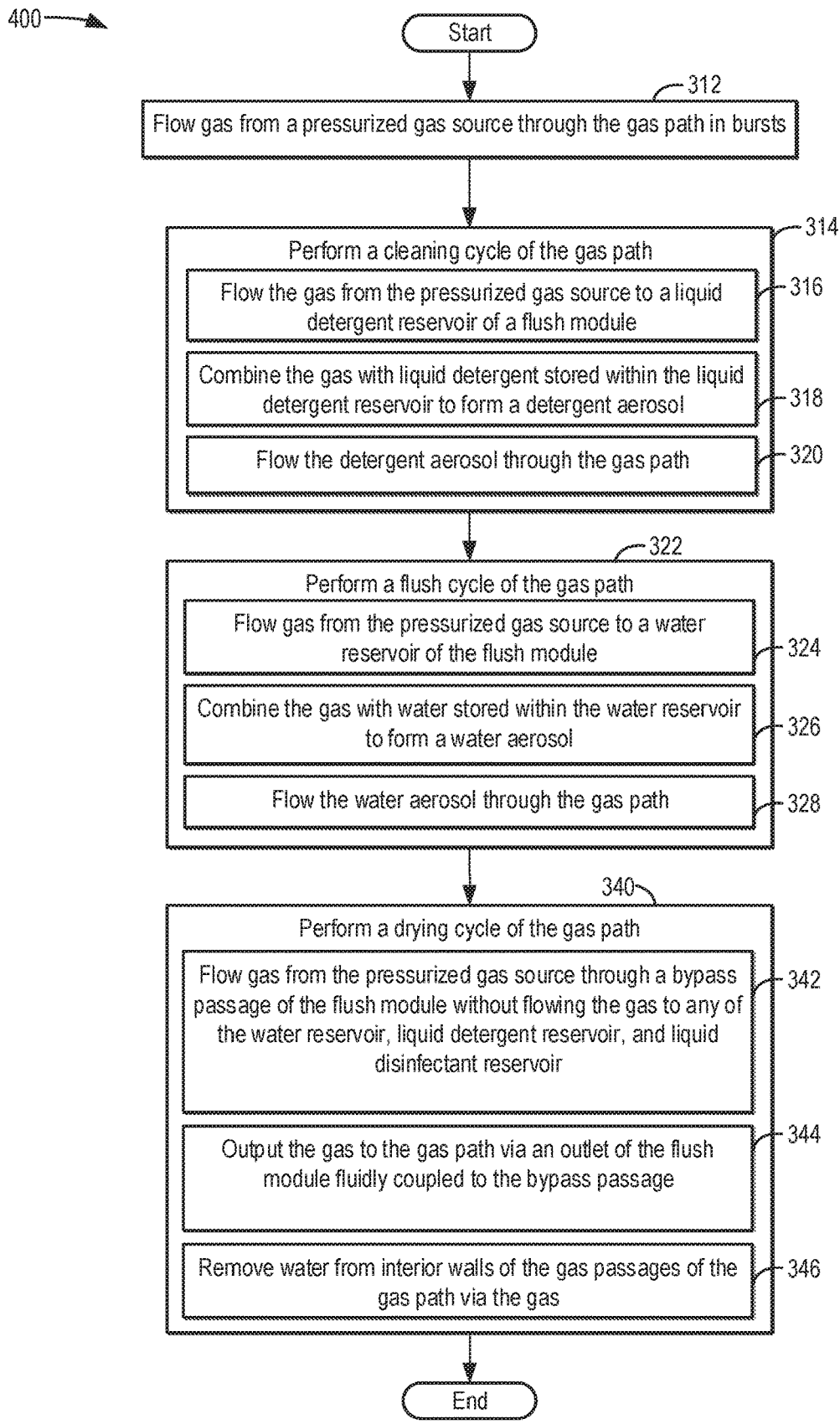

Turning now to FIG. 5, a flowchart illustrating a method 400 for performing cleaning of a gas path of a medical gas flow system including a flush module is shown according to an embodiment of the disclosure. In some embodiments, the cleaning of the gas path described with reference to method 400 may be performed at 206 of method 200 shown by FIG. 4. The medical gas flow system described with reference to method 400 may be similar to the anesthesia machine 99 shown by FIG. 1 and/or the medical gas flow system 100 shown by FIGS. 2-3, and the flush module may be similar to the flush module 66 shown by FIG. 1 and/or the flush module 118 shown by FIGS. 2-3.

At 312, the controller (e.g., similar to controller 62 shown by FIG. 1 and/or controller 199 shown by FIGS. 2-3) may adjust an amount of opening of one or more valves fluidly coupled to the pressurized gas source (e.g., flush module inlet valve 116 shown by FIGS. 2-3) in order to pulse pressurized gases through the gas path. In some embodiments, the controller may move the one or more valves to the fully opened position for a first duration (e.g., 0.5 seconds) and may move the one or more valves to the fully closed position for a second duration (e.g., 1 second), and the first and second duration together may be one pulse (e.g., burst) of the gas flow. The controller may repeat the pulsing for a pre-determined number of pulses, in some embodiments (e.g., five pulses). In other embodiments, the controller may flow gas to the bellows while actuating the bellows (e.g., compressing the bellows) in order to drive gases out of the bellows (e.g., empty the bellows of gases). Emptying the bellows may be performed between each pulse. In other embodiments, the controller may repeat the pulsing until a flow rate of the gas through the gas path is higher than a threshold flow rate, with the flow rate determined by the controller based on an output of a flow rate sensor (e.g., mass flow sensor).

At 314, a cleaning cycle of the gas path is performed. In some embodiments, a pre-determined number of cleaning cycles (e.g., one or more cleaning cycles) may be performed at 314 (e.g., three cleaning cycles). In other embodiments, the controller may determine the number of cleaning cycles based on an operating duration of the medical gas flow path (e.g., an amount of time the medical gas flow path has delivered ventilation gases to a subject since the most recent cleaning cycle). The number of cleaning cycles may be based on a complexity and length of the gas path. In some embodiments, the gas path may be constructed to reduce the number of cycles by providing a short and/or linear gas path.

Performing a cleaning cycle may include, at 316, flowing gas from the pressurized gas source to a liquid detergent reservoir of the flush module. In some embodiments, the liquid detergent reservoir may be a single container of the flush module adapted to receive liquid detergent (e.g., via an opening). In other embodiments, the liquid detergent reservoir may be a removable cartridge adapted to store liquid detergent and fluidly couple with the gas passages of the flush module. Gas may flow to an outlet (e.g., opening) of the liquid detergent reservoir and may come into contact with liquid detergent at the opening.

Performing the cleaning cycle may include, at 318, combining gas with liquid detergent stored within the liquid detergent reservoir to form a detergent aerosol. In some embodiments, the gas is combined with the liquid detergent via a mesh of the flush module (e.g., the mesh 235 described above with reference to FIG. 3). Similar to the example described above with reference to FIG. 3, the pressure of the gas may drive the liquid detergent against the mesh and separate the liquid detergent into fine droplets (e.g., atomize the liquid detergent into a mist). The gas and atomized detergent mist may then mix and/or converge downstream of the mesh to form the detergent aerosol (e.g., the detergent mist may be entrained by the gas).

Performing the cleaning cycle may include, at 320, flowing detergent aerosol through the gas path. In some embodiments, the detergent aerosol may flow through a plurality of valves, gas flow passages, and one or more of a bellows and a bag of the medical gas flow system (e.g., similar to the shaded gas path 171 shown by FIG. 3). Flowing the detergent aerosol through the gas path (e.g., driving the detergent aerosol through the gas path via a pressure of the gas from the gas source) may occur without disassembly of the medical gas flow system (e.g., without removal of the gas passages from the medical gas flow system). The detergent aerosol may come into contact with inner surfaces of the gas passages and other components in order to clean the inner surfaces (e.g., remove debris and/or other accumulations from the inner surfaces). In some embodiments, the detergent aerosol may flow through the flow path to a scavenging system, similar to scavenging system 160 shown by FIGS. 2-3, where the detergent aerosol may be removed from the medical gas flow system for disposal (e.g., not recirculated within the medical gas flow system). Removing the detergent aerosol via the scavenging system may include applying vacuum at an outlet of the gas path (e.g., via a pump, such as pump 156 shown by FIGS. 2-3) in order to increase a flow rate of the detergent aerosol.

At 322, a flush cycle of the gas path is performed. In some embodiments, a pre-determined number of flush cycles (e.g., one or more flush cycles) may be performed at 322 (e.g., four flush cycles). In other embodiments, the controller may determine the number of flush cycles based on a VOC concentration within the gas flow path as measured by the controller via an output of the VOC sensor. A greater VOC concentration may correspond to a higher number of flush cycles (e.g., five cycles) while a lower VOC concentration may correspond to a lower number of flush cycles (e.g., two cycles). The number of flush cycles may be based on a complexity and length of the gas path. In some embodiments, the gas path may be constructed to reduce the number of cycles by providing a short and/or linear gas path.

Performing the flush cycle may include, at 324, flowing gas from the pressurized gas source to a water reservoir of the flush module. In some embodiments, the water reservoir may be a single container of the flush module adapted to receive water (e.g., via an opening). In one embodiment, the water reservoir may be the same reservoir as the detergent reservoir described above, where, prior to filling the water reservoir with water (e.g., distilled water), the liquid detergent is removed from the reservoir. In other embodiments, the water reservoir may be a removable cartridge adapted to store water and fluidly couple with the gas passages of the flush module. Gas may flow to an outlet (e.g., opening) of the water reservoir and may come into contact with water at the opening.

Performing the flush cycle may include, at 326, combining gas with water stored within the water reservoir to form a water aerosol. In some embodiments, the gas is combined with the water via a mesh of the flush module. The mesh may be the same mesh described above at 318. In other embodiments, the mesh at 326 may be a separate mesh from the mesh at 318. Similar to the example described above with reference to FIG. 3, the pressure of the gas may drive the water against the mesh and separate the water into fine droplets (e.g., atomize the water into a mist). The gas and atomized water may then mix and/or converge downstream of the mesh to form the water aerosol (e.g., the water mist may be entrained by the gas).

Performing the flush cycle may include, at 328, flowing the water aerosol through the gas path. In some embodiments, the water aerosol may flow through a plurality of valves, gas flow passages, and one or more of the bellows and the bag of the medical gas flow system (e.g., similar to the shaded gas path 171 shown by FIG. 3). Flowing the water aerosol through the gas path (e.g., driving the water aerosol through the gas path via a pressure of the gas from the gas source) may occur without disassembly of the medical gas flow system (e.g., without removal of the gas passages from the medical gas flow system). The water aerosol may come into contact with inner surfaces of the gas passages and other components in order to flush the inner surfaces (e.g., remove residual detergent from the one or more detergent cycles and/or other accumulations from the inner surfaces). In some embodiments, the water aerosol may flow through the flow path to the scavenging system, where the water aerosol may be removed from the medical gas flow system for disposal (e.g., not recirculated within the medical gas flow system). Removing the water aerosol via the scavenging system may include applying vacuum at an outlet of the gas path (e.g., via a pump, such as pump 156 shown by FIGS. 2-3) in order to increase a flow rate of the water aerosol.

At 340, a drying cycle of the gas path is performed. In some embodiments, a pre-determined number of drying cycles (e.g., one or more drying cycles) may be performed at 340 (e.g., three drying cycles). In other embodiments, the controller may determine the number of drying cycles based on a humidity within the gas flow path as measured by the controller via an output of a humidity sensor. A greater humidity may correspond to a higher number of drying cycles (e.g., five cycles) while a lower humidity may correspond to a lower number of flush cycles (e.g., two cycles). The number of cycles (e.g., drying cycles and/or flush cycles) may be based on a complexity and length of the gas path. In some embodiments, the gas path may be constructed to reduce the number of cycles by providing a short and/or linear gas path.

Performing the drying cycle may include, at 342, flowing gas from the pressurized gas source through a bypass passage of the flush module without flowing the gas to any of the water reservoir, liquid detergent reservoir, and liquid disinfectant reservoir. In some embodiments, the bypass passage may be similar to the bypass gas passage 180 shown by FIGS. 2-3.

Performing the drying cycle may include, at 344, outputting the gas to the gas path via an outlet of the flush module fluidly coupled to the bypass passage. In some embodiments, the outlet may be similar to the outlet 140 shown by FIGS. 2-3.

Performing the drying cycle may include, at 346, removing water from interior walls of the gas passages of the gas path via the gas. The gas flowing through the gas passages may result in evaporation of residual water remaining within the gas passages, and the gas may flow the evaporated water out of the medical gas flow system via the scavenging system. Removing the water via the scavenging system may include applying vacuum at the outlet of the gas path (e.g., via a pump, such as pump 156 shown by FIGS. 2-3) in order to increase a flow rate of the gas and water. Applying vacuum at the outlet of the gas path (e.g., lowering the gas pressure within the gas path) may additionally reduce a temperature at which water evaporates within the gas path, which may increase a removal of water molecules from the gas path and provide an increased amount of drying. Similar to the gas flows described above at 308 and 312, for each drying cycle at 346, the controller may adjust an amount of opening of one or more valves fluidly coupled to the pressurized gas source (e.g., first gas source valve 112 shown by FIGS. 2-3) in order to pulse pressurized gases through the gas path. In some embodiments, the controller may move the one or more valves to the fully opened position for a first duration (e.g., 0.5 seconds) and may move the one or more valves to the fully closed position for a second duration (e.g., 1 second), and the first and second duration together may be one pulse (e.g., burst) of the gas flow. The controller may repeat the pulsing for a pre-determined number of pulses per drying cycle, in some embodiments (e.g., five pulses per drying cycle). In other embodiments, the controller may flow gas to the bellows while actuating the bellows (e.g., compressing the bellows) in order to drive gases out of the bellows (e.g., empty the bellows of gases). Emptying the bellows may be performed between each pulse.

Turning now to FIG. 6, a flowchart illustrating method 500 for performing disinfecting of a gas path of a medical gas flow system including a flush module is shown according to an embodiment of the disclosure. In some embodiments, the disinfecting of the gas path described with reference to method 500 may be performed at 210 of method 200 shown by FIG. 4. The medical gas flow system described with reference to method 500 may be similar to the anesthesia machine 99 shown by FIG. 1 and/or the medical gas flow system 100 shown by FIGS. 2-3, and the flush module may be similar to the flush module 66 shown by FIG. 1 and/or the flush module 118 shown by FIGS. 2-3.

At 308, gas flows through the gas path in bursts. Similar to the gas flow described above with reference to 312 of method 400 of FIG. 5, the controller may adjust the amount of opening of one or more valves fluidly coupled to the pressurized gas source (e.g., first gas source valve 112 shown by FIGS. 2-3) in order to pulse pressurized gases through the gas path.

At 332, a disinfecting cycle of the gas path is performed. In some embodiments, a pre-determined number of disinfecting cycles (e.g., one or more disinfecting cycles) may be performed at 332 (e.g., three disinfecting cycles). In other embodiments, the controller may determine the number of disinfecting cycles based on an operating duration of the medical gas flow path (e.g., an amount of time the medical gas flow path has delivered ventilation gases to a subject since the most recent disinfecting cycle). The number of disinfecting cycles may be based on a complexity and length of the gas path. In some embodiments, the gas path may be constructed to reduce the number of cycles by providing a short and/or linear gas path.

Performing the disinfecting cycle may include, at 334, flowing gas from the pressurized gas source to a liquid disinfectant reservoir of the flush module. In some embodiments, the liquid disinfectant reservoir may be a single container of the flush module adapted to receive liquid disinfectant (e.g., via an opening). In one embodiment, the liquid disinfectant reservoir may be the same reservoir as the detergent reservoir and/or water reservoir described above with reference to FIGS. 4-5, where, prior to filling the liquid disinfectant reservoir with liquid disinfectant (e.g., CIDEX® OPA Solution), the water and/or liquid detergent is removed from the reservoir. In other embodiments, the liquid disinfectant reservoir may be a removable cartridge adapted to store liquid disinfectant and fluidly couple with the gas passages of the flush module. Gas may flow to an outlet (e.g., opening) of the liquid disinfectant reservoir and may come into contact with liquid disinfectant at the opening. In some embodiments, the liquid disinfectant may instead be a disinfectant stored in a gaseous state, or the liquid disinfectant may be heated in order to become vaporized for delivery through the gas path by the pressurized gas source.

Performing the disinfecting cycle may include, at 336, combining the gas with liquid disinfectant stored within the liquid disinfectant reservoir to form a disinfectant aerosol. In some embodiments, the gas is combined with the liquid disinfectant via a mesh of the flush module. In some embodiments, the mesh may be the same mesh described above with reference to FIG. 5 at 318 and/or 326. In other embodiments, the mesh at 336 may be a separate mesh from the mesh at 318 and/or 326. Similar to the example described above with reference to FIG. 3, the pressure of the gas may drive the liquid disinfectant against the mesh and separate the liquid disinfectant into fine droplets (e.g., atomize the liquid disinfectant into a mist). The gas and atomized disinfectant may then mix and/or converge downstream of the mesh to form the disinfectant aerosol (e.g., the disinfectant mist may be entrained by the gas).

Performing the disinfecting cycle may include, at 338, flowing the disinfectant aerosol through the gas path. In some embodiments, the disinfectant aerosol may flow through one or more valves (e.g., inhalation flow valve 162, check valve 142, check valve 146, etc.), gas flow passages, and one or more of the bellows (e.g., bellows 152 shown by FIGS. 2-3) and the bag (e.g., bag 154 shown by FIGS. 2-3) of the medical gas flow system (e.g., similar to the shaded gas path 171 shown by FIG. 3). Flowing the disinfectant aerosol through the gas path (e.g., driving the disinfectant aerosol through the gas path via a pressure of the gas from the gas source) may occur without disassembly of the medical gas flow system (e.g., without removal of the gas passages from the medical gas flow system). The disinfectant aerosol may come into contact with inner surfaces of the gas passages and other components in order to disinfect the inner surfaces (e.g., remove biological contaminants from the inner surfaces). In some embodiments, the disinfectant aerosol may flow through the flow path to the scavenging system, where the disinfectant aerosol may be removed from the medical gas flow system for disposal (e.g., not recirculated within the medical gas flow system). Removing the disinfectant aerosol via the scavenging system may include applying vacuum at an outlet of the gas path (e.g., via a pump, such as pump 156 shown by FIGS. 2-3) in order to increase a flow rate of the disinfectant aerosol.

At 333, a flush cycle of the gas path is performed. In some embodiments, a pre-determined number of flush cycles (e.g., one or more flush cycles) may be performed at 333 (e.g., four flush cycles). In other embodiments, the controller may determine the number of flush cycles based on a VOC concentration within the gas flow path as measured by the controller via an output of the VOC sensor. A greater VOC concentration may correspond to a higher number of flush cycles (e.g., five cycles) while a lower VOC concentration may correspond to a lower number of flush cycles (e.g., two cycles). The controller may compare the VOC concentration to a threshold VOC concentration in some embodiments. The threshold VOC concentration may be a function of patient parameters (e.g., age, weight, etc.) in some embodiments. In other embodiments, the threshold VOC concentration may be a pre-determined concentration value stored in a memory of the controller.

Performing the flush cycle may include, at 335, flowing gas from the pressurized gas source to a water reservoir of the flush module. In some embodiments, the water reservoir may be a single container of the flush module adapted to receive water (e.g., via an opening). In one embodiment, the water reservoir may be the same reservoir as the liquid disinfectant reservoir described above, where, prior to filling the liquid disinfectant reservoir with water (e.g., distilled water), the liquid disinfectant is removed from the reservoir. In other embodiments, the water reservoir may be a removable cartridge adapted to store water and fluidly couple with the gas passages of the flush module. Gas may flow to an outlet (e.g., opening) of the water reservoir and may come into contact with water at the opening.

Performing the flush cycle may include, at 337, combining gas with water stored within the water reservoir to form a water aerosol. In some embodiments, the gas is combined with the water via a mesh of the flush module. The mesh may be the same mesh described above at 336. In other embodiments, the mesh at 326 may be a separate mesh from the mesh at 336. Similar to the example described above with reference to FIG. 3, the pressure of the gas may drive the water against the mesh and separate the water into fine droplets (e.g., atomize the water into a mist). The gas and atomized water may then mix and/or converge downstream of the mesh to form the water aerosol (e.g., the water mist may be entrained by the gas).

Performing the flush cycle may include, at 339, flowing the water aerosol through the gas path. In some embodiments, the water aerosol may flow through a plurality of valves, gas flow passages, and one or more of the bellows and the bag of the medical gas flow system (e.g., similar to the shaded gas path 171 shown by FIG. 3). Flowing the water aerosol through the gas path (e.g., driving the water aerosol through the gas path via a pressure of the gas from the gas source) may occur without disassembly of the medical gas flow system (e.g., without removal of the gas passages from the medical gas flow system). The water aerosol may come into contact with inner surfaces of the gas passages and other components in order to flush the inner surfaces (e.g., remove residual detergent from the one or more detergent cycles and/or other accumulations from the inner surfaces). In some embodiments, the water aerosol may flow through the flow path to the scavenging system, where the water aerosol may be removed from the medical gas flow system for disposal (e.g., not recirculated within the medical gas flow system). Removing the water aerosol via the scavenging system may include applying vacuum at an outlet of the gas path (e.g., via a pump, such as pump 156 shown by FIGS. 2-3) in order to increase a flow rate of the water aerosol.

At 341, a drying cycle of the gas path is performed. In some embodiments, a pre-determined number of drying cycles (e.g., one or more drying cycles) may be performed at 341 (e.g., three drying cycles). In other embodiments, the controller may determine the number of drying cycles based on a humidity within the gas flow path as measured by the controller via an output of a humidity sensor. A greater humidity may correspond to a higher number of drying cycles (e.g., five cycles) while a lower humidity may correspond to a lower number of flush cycles (e.g., two cycles). The number of drying cycles may be based on a complexity and length of the gas path. In some embodiments, the gas path may be constructed to reduce the number of cycles by providing a short and/or linear gas path.

Performing the drying cycle may include, at 343, flowing gas from the pressurized gas source through a bypass passage of the flush module without flowing the gas to any of the water reservoir, liquid detergent reservoir, and liquid disinfectant reservoir. In some embodiments, the bypass passage may be similar to the bypass gas passage 180 shown by FIGS. 2-3.

Performing the drying cycle may include, at 345, outputting the gas to the gas path via an outlet of the flush module fluidly coupled to the bypass passage. In some embodiments, the outlet may be similar to the outlet 140 shown by FIGS. 2-3.

Performing the drying cycle may include, at 347, removing water from interior walls of the gas passages of the gas path via the gas. The gas flowing through the gas passages may result in evaporation of residual water remaining within the gas passages, and the gas may flow the evaporated water out of the medical gas flow system via the scavenging system. Removing the water via the scavenging system may include applying vacuum at the outlet of the gas path (e.g., via a pump, such as pump 156 shown by FIGS. 2-3) in order to increase a flow rate of the gas and water. Similar to the gas flows described above at 308 and 312, for each drying cycle at 346, the controller may adjust an amount of opening of one or more valves fluidly coupled to the pressurized gas source (e.g., first gas source valve 112 shown by FIGS. 2-3) in order to pulse pressurized gases through the gas path. In some embodiments, the controller may move the one or more valves to the fully opened position for a first duration (e.g., 0.5 seconds) and may move the one or more valves to the fully closed position for a second duration (e.g., 1 second), and the first and second duration together may be one pulse (e.g., burst) of the gas flow. The controller may repeat the pulsing for a pre-determined number of pulses per drying cycle, in some embodiments (e.g., five pulses per drying cycle). In other embodiments, the controller may flow gas to the bellows while actuating the bellows (e.g., compressing the bellows) in order to drive gases out of the bellows (e.g., empty the bellows of gases). Emptying the bellows may be performed between each pulse.

Figure 7:
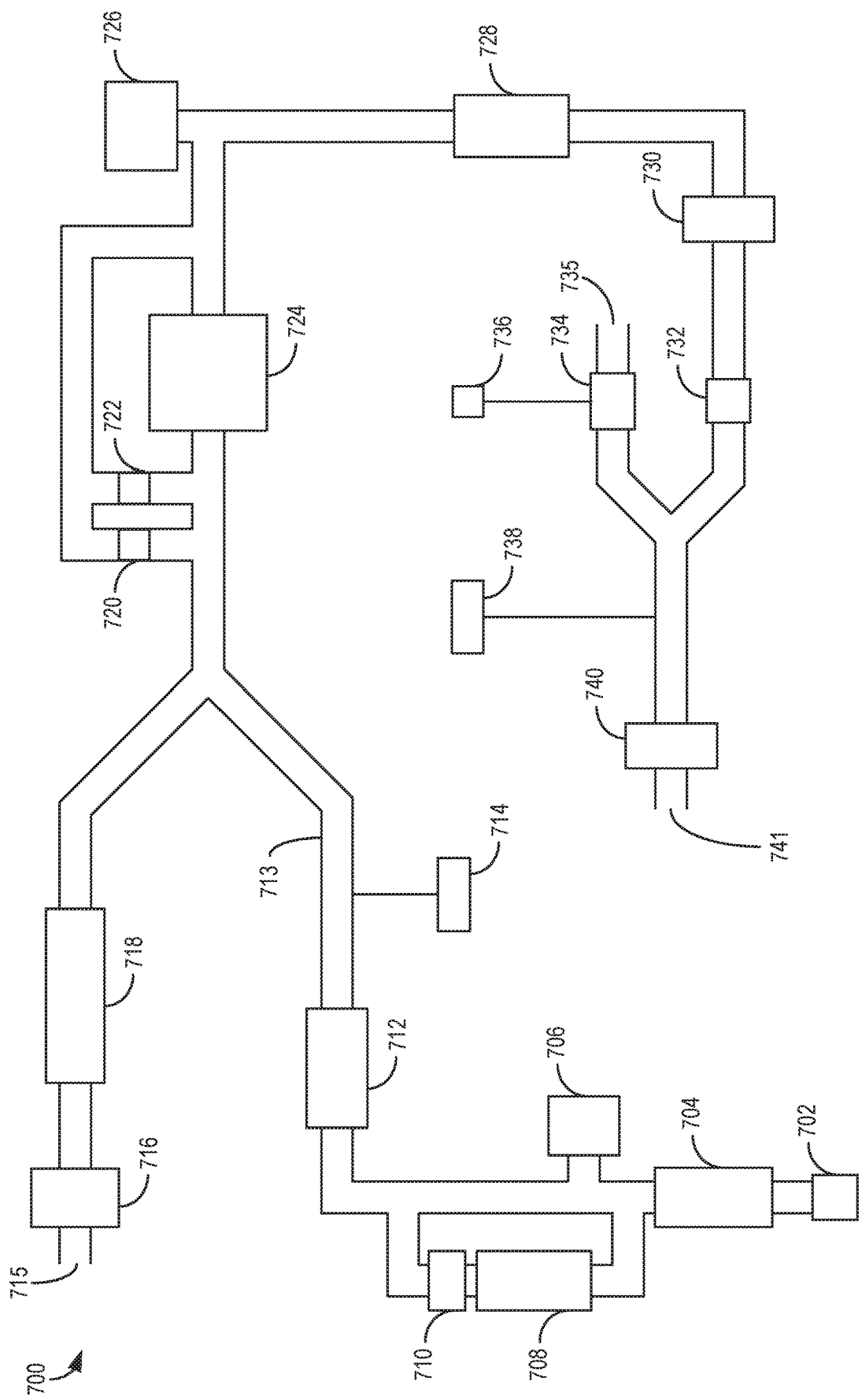

Referring now to FIG. 7, medical gas flow system 700 is shown. Medical gas flow system 700 may be utilized as a ventilator in some examples, wherein air and oxygen are mixed prior to being delivered to a patient. Medical gas flow system 700 includes a flush module 710, similar to the flush modules described above (e.g., flush module 66, flush module 118). The flush module 710 may perform one or more flush cycles, cleaning cycles, disinfecting cycles, and/or drying cycles of the gas flow path of the medical gas flow system 700, similar to the embodiments described above. Further, medical gas flow system 700 may include several components similar to those included by the medical gas flow systems described above. For example, medical gas flow system 700 includes flush module inlet valve 708 which may be similar to flush module inlet valve 116 described above, oxygen inlet port 702 which may be similar to first gas source 102 described above, etc.

Medical gas flow system 700 may additionally include regulator 704 and proportional valve 712 for adjusting a pressure of oxygen flowing through gas passages 713 of the medical gas flow system 700. Regulator 704 and/or proportional valve 712 may be controlled (e.g., adjusted) by a controller of the medical gas flow system 700 in some embodiments (e.g., with the controller being similar to controller 199 described above). Medical gas flow system 700 may further include oxygen pressure switch 706, oxygen flow sensor 714, air inlet 715 (e.g., for receiving air to be mixed with oxygen from oxygen inlet port 702), air inlet filter 716, and muffler 718.

The medical gas flow system 700 includes blower 724 (e.g., a turbine) configured to increase a pressure of gases within the gas passages forming the gas flow path of the medical gas flow system 700. Blower 724 may additionally mix and/or converge gases from the air inlet 715 and the oxygen inlet port 702 (e.g., to form a mixture of air and oxygen for respiration by a patient). During conditions in which a pressure of gases downstream of the blower 724 exceeds a threshold pressure, one or each of the first bypass valve 720 and second bypass valve 722 may open responsive to the gas pressure in order to reduce the pressure of gases delivered to the patient (e.g., the gases downstream of the blower 724). Further, a speed of blower 724 may be adjusted by the controller of the medical gas flow system 700 in order to adjust the flow rate and/or pressure of gases downstream of the blower 724.

Gases (e.g., mixed air and oxygen) flowing from the blower 724 through the gas passages may flow across oxygen sensor 726, and oxygen sensor 726 may output signals indicating a measured oxygen concentration of the gases to the controller. The gases may flow through muffler 728, bacterial filter 730, check valve 732, and filter 740 for inhalation by a patient at patient inlet/outlet 741. Exhalation gases from the patient may flow through the gas passages through exhalation valve 734 to exhalation outlet 735. A pressure of the exhalation gases may be measured by pressure sensor 736 (e.g., with pressure sensor 736 configured to transmit the measured pressure electronically to the controller). A flow rate of inhalation gases to the patient inlet/outlet 741 and exhalation gases from the patient inlet/outlet 741 may be measured by flow sensor 738, and flow sensor 738 may transmit the measured flow rate electronically to the controller.

During conditions in which the flush module 710 is used to perform one or more cleaning cycles of the gas flow path of the medical gas flow system 700, the flush module 710 may flow detergent through several components positioned downstream of the flush module 710 without disconnecting or removing components from the medical gas flow system 700. For example, detergent may flow through or across check valve 732, flow sensor 738, exhalation valve 734, etc. in order to clean the components. Similarly, when performing one or more disinfecting cycles of the gas flow path, the flush module 710 may flow disinfectant to the components in order to disinfect the components. When performing one or more flush cycles of the gas flow path, the flush module 710 may flow water to the components in order to flush the components, and when performing one or more drying cycles of the gas flow path, the flush module may flow gases (e.g., air or and/or oxygen) to the components in order to dry the components. The cleaning cycles, disinfecting cycles, flush cycles, and drying cycles may be similar to those described above with reference to FIGS. 4-6, in some embodiments. In some embodiments, flowing detergent, disinfectant, and water through the gas flow path may include not recirculating the detergent, disinfectant, and water through the medical gas flow system 700 (e.g., disposing of the used detergent, disinfectant, and water at exhalation outlet 735 of the medical gas flow system 700).

The technical effect of flowing pressurized gas to the liquid reservoir of the flush module is to perform the cleaning and/or disinfecting of the gas flow path of the medical gas flow system without disassembling the medical gas flow system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical gas flow system, comprising:
performing a disinfecting cycle of a ventilation gas path comprising a plurality of gas flow passages by:
flowing gas from a pressurized gas source of the medical gas flow system to a liquid disinfectant reservoir of a flush module;
combining the gas with a liquid disinfectant stored within the liquid disinfectant reservoir to form a disinfectant aerosol; and
flowing the disinfectant aerosol through the plurality of gas flow passages; and
performing a flush cycle of the ventilation gas path by:
flowing the gas from the pressurized gas source of the medical gas flow system to a water reservoir of the flush module;
combining the gas with water stored within the water reservoir to form a water aerosol; and
flowing the water aerosol through the plurality of gas flow passages.

2. The method of claim 1, wherein flowing gas from the pressurized gas source of the medical gas flow system to the liquid disinfectant reservoir of the flush module includes flowing the gas through a vaporizer bypass passage, and wherein flowing the disinfectant aerosol through the plurality of gas flow passages includes flowing the disinfectant aerosol from an outlet of the flush module to the plurality of gas flow passages, the outlet positioned downstream of a vaporizer.

3. The method of claim 1, wherein flowing the gas from the pressurized gas source of the medical gas flow system to the liquid disinfectant reservoir includes flowing the gas at a pressure above atmospheric air pressure to an inlet of the flush module, the inlet fluidly coupled to the liquid disinfectant reservoir.

4. The method of claim 3, wherein flowing the disinfectant aerosol through the plurality of gas flow passages includes driving the disinfectant aerosol through the plurality of gas flow passages via the pressure of the gas from the pressurized gas source.

5. The method of claim 1, wherein combining the gas with the liquid disinfectant stored within the liquid disinfectant reservoir includes producing a disinfectant mist from the liquid disinfectant and entraining the disinfectant mist with the gas.

6. The method of claim 5, wherein producing the disinfectant mist includes driving the liquid disinfectant through a mesh via a pressure of the gas.

7. The method of claim 1, wherein performing the flush cycle occurs immediately after performing the disinfecting cycle with no other cycles therebetween, and further comprising:
while performing the flush cycle, measuring a concentration of volatile organic chemicals (VOCs) disposed within at least one gas passage of the plurality of gas flow passages at an outlet of the ventilation gas path; and
responsive to the concentration of VOCs, repeating the flush cycle or performing a drying cycle of the ventilation gas path.

8. The method of claim 7, wherein the drying cycle comprises:
flowing the gas from the pressurized gas source of the medical gas flow system through a bypass passage of the flush module without flowing the gas to either of the water reservoir or the liquid disinfectant reservoir;

outputting the gas to the plurality of gas passages via a flush module outlet fluidly coupled to the bypass passage; and removing water from interior walls of the plurality of gas flow passages via the gas.

9. The method of claim 1, further comprising:

performing a cleaning cycle of the ventilation gas path by:
flowing the gas from the pressurized gas source of the medical gas flow system to a liquid detergent reservoir of the flush module;

combining the gas with a liquid detergent stored within the liquid detergent reservoir to form a detergent aerosol; and flowing the detergent aerosol through the plurality of gas flow passages.

10. The method of claim 9, wherein combining the gas with the liquid detergent stored within the liquid detergent reservoir includes producing a detergent mist from the liquid detergent by driving the liquid detergent through a mesh via a pressure of the gas and entraining the detergent mist with the gas.

11. The method of claim 9, wherein the disinfecting cycle additionally comprises flowing the disinfectant aerosol through each of a bellows and at least one valve positioned in the ventilation gas path of the medical gas flow system, and wherein the cleaning cycle additionally comprises flowing the detergent aerosol through each of the bellows and the at least one valve.

12. The method of claim 9, wherein performing the cleaning cycle occurs immediately prior to performing the flush cycle with no other cycles therebetween, and wherein performing the disinfecting cycle occurs after performing the flush cycle.

13. The method of claim 12, further comprising performing at least one additional flush cycle following the disinfecting cycle.

14. A method, comprising:

during a first condition, flowing inhalation gas from a gas source to a patient breathing apparatus through a plurality of gas flow passages coupled together to form a ventilation gas path of a medical gas flow system while bypassing a flush module fluidly coupled to the plurality of gas flow passages, and flowing exhalation gas through a subset of the plurality of gas flow passages from the patient breathing apparatus;

during a second condition and without decoupling the plurality of gas flow passages after flowing the exhalation gas through the plurality of gas flow passages during the first condition, flowing the gas from the gas source to a liquid disinfectant reservoir of the flush module, combining the gas with a liquid disinfectant stored within the liquid disinfectant reservoir to form a disinfectant aerosol, and flowing the disinfectant aerosol through at least the subset of the plurality of gas flow passages; and during a third condition, flowing the gas from the gas source to a water reservoir of the flush module, combining the gas with water stored within the water reservoir to form a water aerosol, and flowing the water aerosol through at least the subset of the plurality of gas flow passages.

15. The method of claim 14, wherein the first condition includes operating the medical gas flow system with the patient breathing apparatus coupled to a patient, the second condition includes operating the medical gas flow system with the patient breathing apparatus decoupled from the patient, and wherein the method further comprises:

first, flowing a detergent from the flush module through at least the subset of the plurality of gas flow passages;

then, flowing the water aerosol from the flush module through at least the subset of the plurality of gas flow passages; and then, flowing the disinfectant aerosol from the flush module through at least the subset of the plurality of gas flow passages.

* * * * *